United States Patent [19]
Peroutka

[11] Patent Number: 5,879,884
[45] Date of Patent: Mar. 9, 1999

[54] DIAGNOSIS OF DEPRESSION BY LINKAGE OF A POLYMORPHIC MARKER TO A SEGMENT OF CHROMOSOME 19P13 BORDERED BY D19S247 AND D19S394

[76] Inventor: Stephen J. Peroutka, 1025 Tournament Dr., Hillsborough, Calif. 94010

[21] Appl. No.: 482,180

[22] Filed: Jun. 7, 1995

Related U.S. Application Data

[63] Continuation-in-part of Ser. No. 366,288, Dec. 29, 1994, abandoned.
[51] Int. Cl.[6] .............................. C12Q 1/68; C12P 19/34; C07H 21/02; C07H 21/04
[52] U.S. Cl. .................................. 435/6; 435/91.2; 435/5; 536/24.3; 536/24.31; 536/24.32; 536/24.33
[58] Field of Search .................................. 435/6, 5, 91.2; 536/24.3, 24.31, 24.32, 24.33

[56] References Cited

PUBLICATIONS

Sommer et al, "Minimal homology requirements for PCR primers", Nucleic Acids Res. 17(16):6749, Aug. 1989.
Law et al, "Genetic linkage analysis of bipolar affective disorder in an old order amish pedigree", Hum. Genet. 88:562–568, Mar. 1992.
Egeland et al, "Bipolar affective disorders linked to DNA markers on chromosome 11", Nature 325:783–787, Feb. 1987.
Perkin Elmer Cetus, "GeneAmp DNA amplification reagent kit" Oct. 1988.
Weber et al, "Dinucleotide repeat polymorphism at the D19S76 locus", Nucleic Acids Res. 18(9):2835, May 1990.
Mitchell et al, "Close linkage of bipolar disorder to chromosome 11 markers is excluded in two large australian pedigrees", J. Aff. Disord. 21:23–32, Jan. 1991.
Kawada et al, "No evidence of linkage or association between tyrosine hydroxylase gene and affective disorder", J. Aff. Disord. 34:89–94, May 1991.

Straub et al, "Genetic Linkage studies of Bipolar Affective Disorder" in Genome Maps and Neurological Disorders (Davies and Tilghman eds) Cold Spring Harbor Laboratory Press, Cold Spring Harbor, New York, pp. 77–99, 1993.
Stewart et al., "Migraine headache: epidemiology and health care utilization," *Cephalalgia Suppl* 12, 41–46 (1993).
Breslau et al., "Migraine, Psychiatric Disorders, and Suicide Attempts: An Epidemiologic Study of Young Adults," *Psychiatry Research* 37, 11–23 (1991).
Lazarou et al., "Huntington's disease: predictive testing and the molecular genetics laboratory," *Clinical Genetics* 9, 150–156 (1993).
Cotton, "Current methods of mutation detection," *Mutation Research* 285, 125–144 (1993).
Breslau et al., "Comorbidity of migraine and major affective disorders," *Neurology* 44, 17–22 (1994).
Peroutka et al., "The Clinical Utility of Pharmacological Agents That Act at Serotonin Receptors," *Journal of Neuropsychiatry* 1, 253–262 (1989).
Hudson et al., "Affective Spectrum Disorder: Does Antidepressant Response Identify a Family of Disorders With a Common Pathophysiology?," *Am J Psychiatry* 147, 552–564 (1990).
Joutel et al., "A gene for familial hemiplegic migraine maps to chromosome 19," *Nature Genetics* 5, 40–45 (1993).
Ophoff et al., "Genetic Heterogeneity of Familial Hemiplegic Migraine," *Genomics* 22, (1994 preprint).
Pericak–Vance, "Analysis of Genetic Linkage Data," in (eds. Dracopoli et al., Wiley, 1994), Unit 1.4.

*Primary Examiner*—George C. Elliott
*Assistant Examiner*—Jeffrey Fredman
*Attorney, Agent, or Firm*—Townsend & Townsend & Crew

[57] ABSTRACT

The invention maps a gene (dep) associated with depression to the p13 region of chromosome 19. The invention exploits this discovery to provide methods of diagnosing depression, methods of screening for the dep gene, and libraries of cloned segments including the dep gene.

19 Claims, 14 Drawing Sheets

DIAGNOSIS OF DEPRESSION BY LINKAGE OF A POLYMORPHIC MARKER TO A SEGMENT OF CHROMOSOME 19P13 BORDERED BY D19S247 AND D19S394

This application is a continuation-in-part of U.S. Ser. No. 08/366,288, filed Dec. 29, 1994 (now abandoned).

TECHNICAL FIELD

The present invention relates generally to the diagnosis and treatment of depression.

BACKGROUND OF THE INVENTION

Depression is a clinical disorder that may begin at any age, although it usually begins in the mid-20s and 30s. The Diagnostic and Statistical Manual-IV (DSM-IV) criteria used to diagnose depression are provided in Table 1. These symptoms may develop over days to weeks. Some people have only a single episode, with a full return to premorbid function. However, more than 50 percent of those who initially suffer a single major depressive episode eventually develop another.

The point prevalence for major depressive disorder in the Western industrialized nations is 2.3 to 3.2 percent for men and 4.5 to 9.3 percent for women. The lifetime risk for major depressive disorder is 7 to 12 percent for men and 20 to 25 percent for women. Risk factors for major depressive disorder include female gender (especially during the postpartum period), a history of depressive illness in first-degree relatives and prior episodes of major depression. Patients with major depressive disorder have substantial amounts of physical and psychological disability, as well as occupational difficulties. Untreated major depressive disorder has a substantial effect on health and functioning. Physical complaints are also common during a major depressive episode.

Although a genetic component has been suggested in depression, it has not been confirmed, much less characterized (U.S. Department of Health and Human Services; AHCPR Publication No. 93-0550, 1993). Further, it has not been reported whether the genetic bases and corresponding biochemical mechanisms underlying the different forms of depression are different in kind or only in degree. At present no specific genetic or biochemical tests are available for the positive diagnosis of depression. Diagnosis and treatment is presently based solely on patient self-reporting and symptom description. The clinical heterogeneity associated with depression has complicated patient reporting as well as the diagnosis and treatment of the disorder. As a result, no clear modality of treatment for all individuals with depression has emerged, and treatment as well as diagnosis varies greatly not only from patient to patient but from physician to physician. Thus, many sufferers of depression are not diagnosed or not effectively treated.

Identification of inheritance pattern(s) and genetic bases for depression would greatly facilitate the diagnosis and treatment of this disorder. The present invention fulfills this and other needs by mapping a gene associated with an increase in susceptibility to depression to a region within chromosome 19.

SUMMARY OF THE INVENTION

The invention provides methods of diagnosing a patient having depression. Some methods determine the presence or absence of an allele of a linked polymorphic marker in the DNA of the patient. The polymorphic marker is within chromosome 19p13 and is linked to a gene (dep) having a variant form associated with a phenotype of depression. The allele of the polymorphic marker detected in these methods is in phase with the variant form of the dep gene. Thus, the presence of the allele in the patient indicates susceptibility to depression. Closely linked polymorphic markers occur between D19S247 and D19S244. A preferred marker is D19S391.

Some methods comprise an additional step of determining the phase of the allele of the polymorphic marker detected in the patient with respect to the variant form of the dep gene, which leads to a depression phenotype. Phase can be established by determining the presence or absence of the allele in two relatives of the patient, who should preferably be relatives of the first or second degree. The relatives should each be of known phenotype with respect to depression. At least one of the relatives should have depression, and that relative should also be heterozygous for the allele. The phenotype of relatives can be determined from the criteria of the Diagnostic and Statistical Manual IV shown in Table 1 as well as from the Clinical Rating Scale for Depression (Table 2).

In other methods of diagnosis, susceptibility to depression in a patient is determined by analyzing a relative of the patient for a phenotype of depression. These methods are particularly useful when the patient is presently asymptomatic or exhibiting marginal symptoms.

The invention further provides kits for diagnosis of depression. Such a kit comprises an oligonucleotide which hybridizes to a DNA segment within chromosome 19p13, the DNA segment being linked to the dep gene. Preferably, the oligonucleotide hybridizes to a DNA segment between D19S247 and D19S244. Some kits comprise paired first and second oligonucleotides for amplification of a target segment DNA. The first and second oligonucleotides serve to prime amplification of a target DNA segment between D19S247 and D19S244. Other kits comprise paired first and second oligonucleotides respectively hybridizing to first and second allelic variants of the DNA segment. Such kits are useful for e.g., ASO analysis or allele-specific PCR.

The invention further provides methods of screening for the dep gene. In these methods, a first polymorphic marker is selected between positions D19S247 and D19S244 of chromosome 19. A linkage distance is then determined between the first polymorphic marker and the gene. A further polymorphic marker is selected within the linkage distance of the previous marker, and a linkage distance is determined between the further polymorphic marker and the gene. The process of selecting polymorphic markers and determining linkage distance is then repeated as necessary until the dep gene is localized to a segment of about 1, 2 or 5 Mb.

The invention further provides libraries enriched for clones from the region of chromosome 19p13 containing the dep gene. The libraries consist essentially of a plurality of vectors each encoding a segment of DNA between D19S247 and D19S244.

Definitions

Figure 1A:
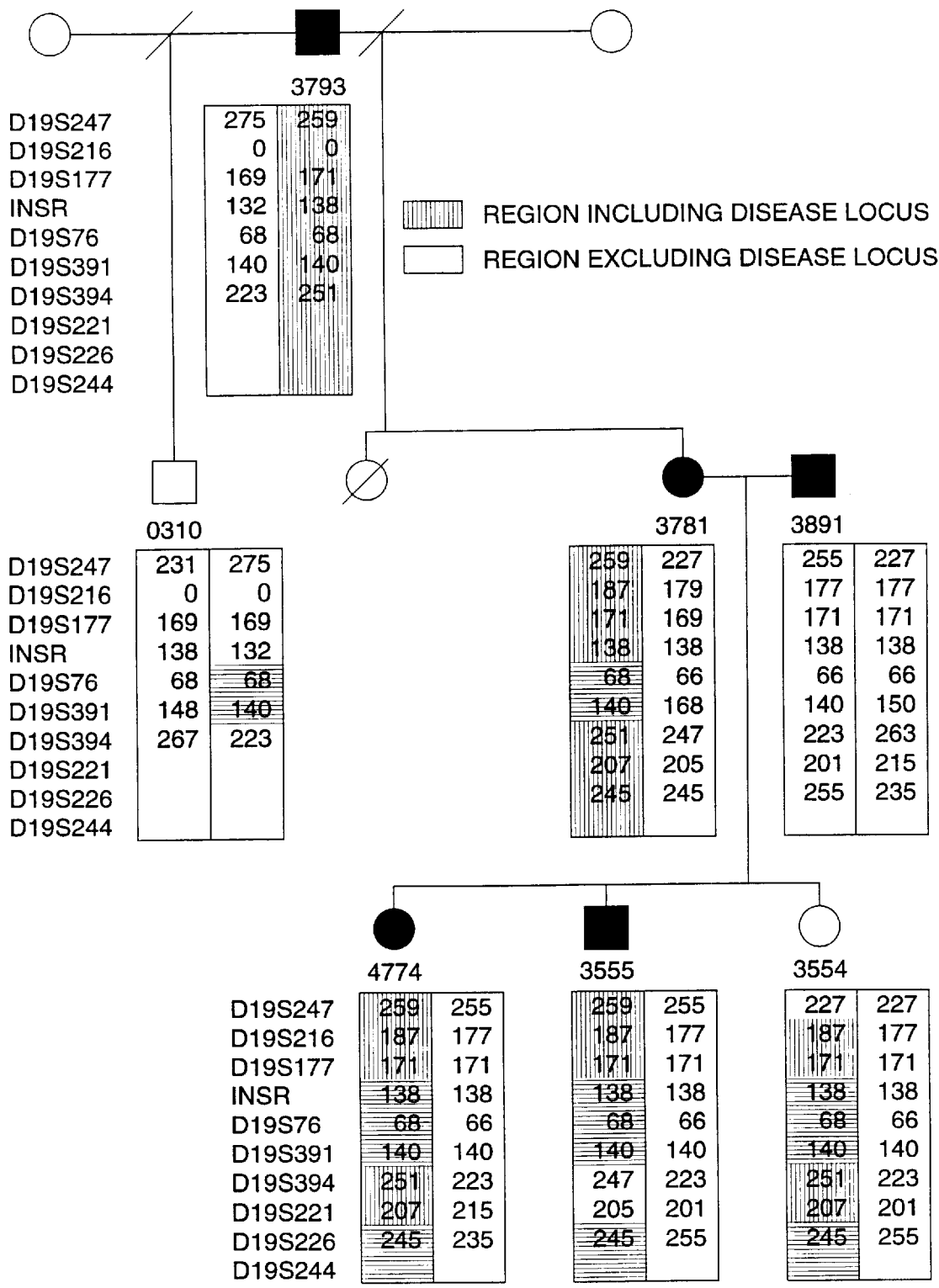
FIG. 1 Panels A–J. Haplotype analysis of dep segregation with polymorphic markers in 10 families (panels A–J, respectively). An upward arrow indicates distal localization of the dep gene and a downward arrow indicates proximal localization of the dep gene.
Figure 1B:
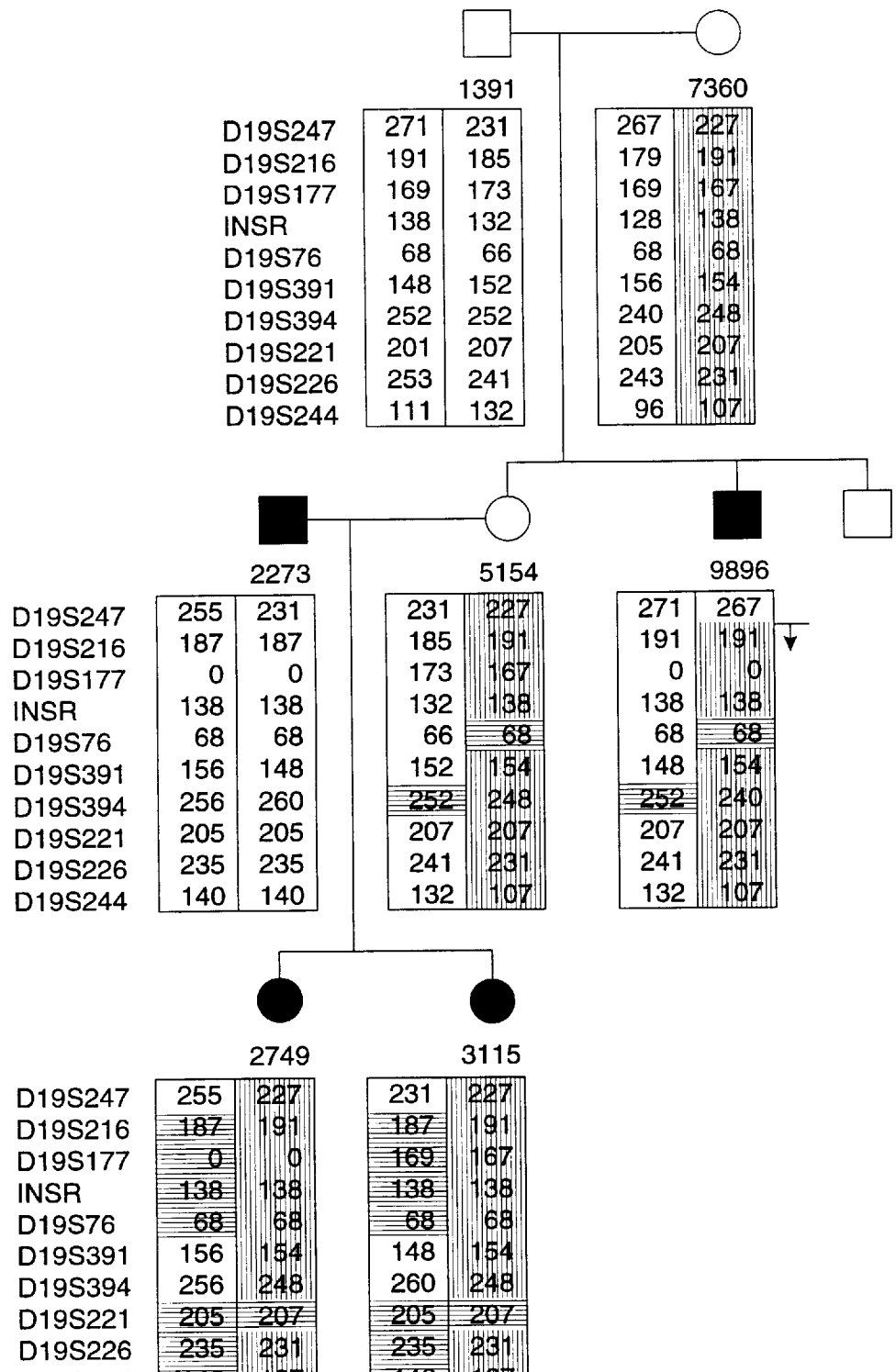
Figure 1C:
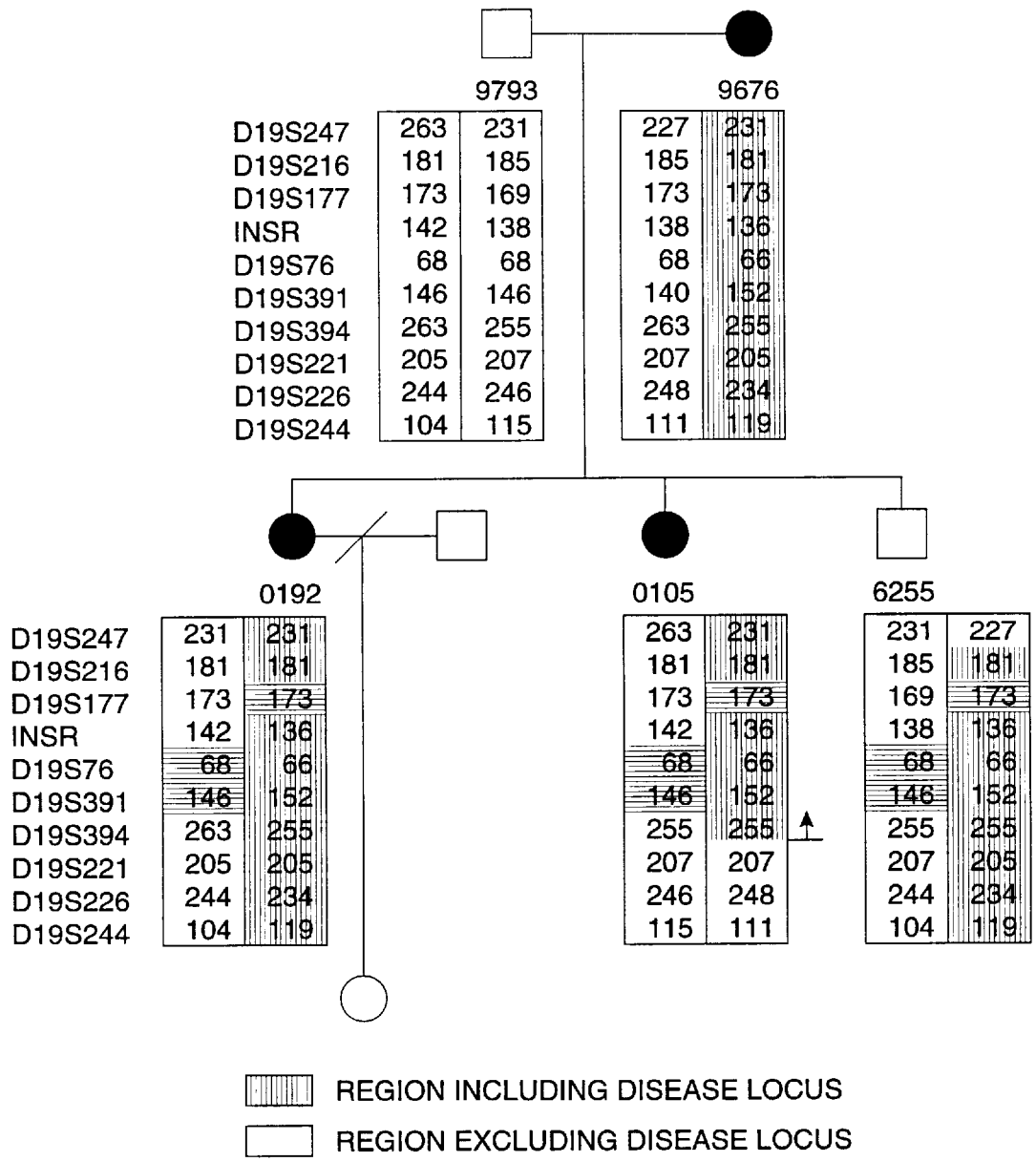
Figure 1D:
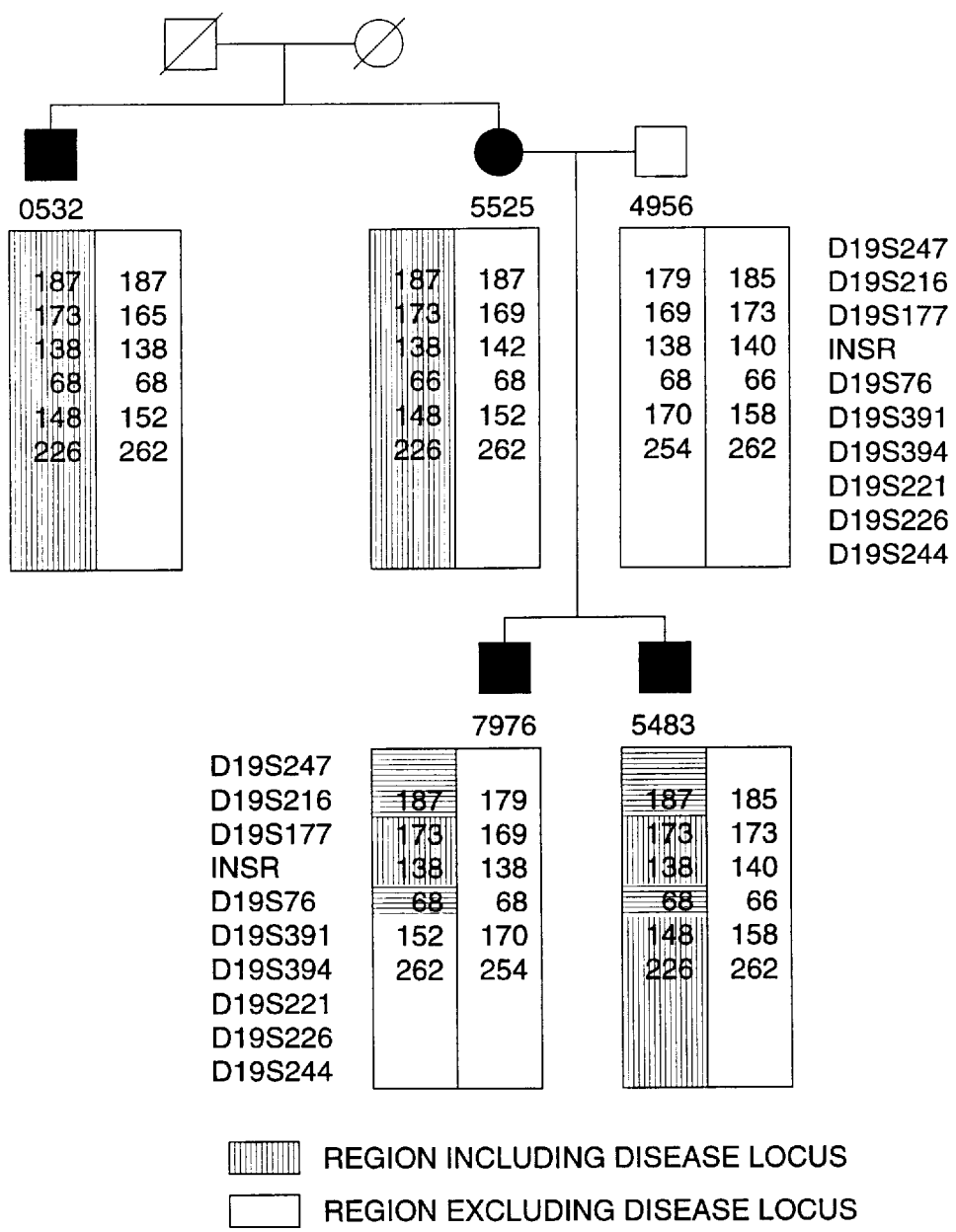
Figure 1E:
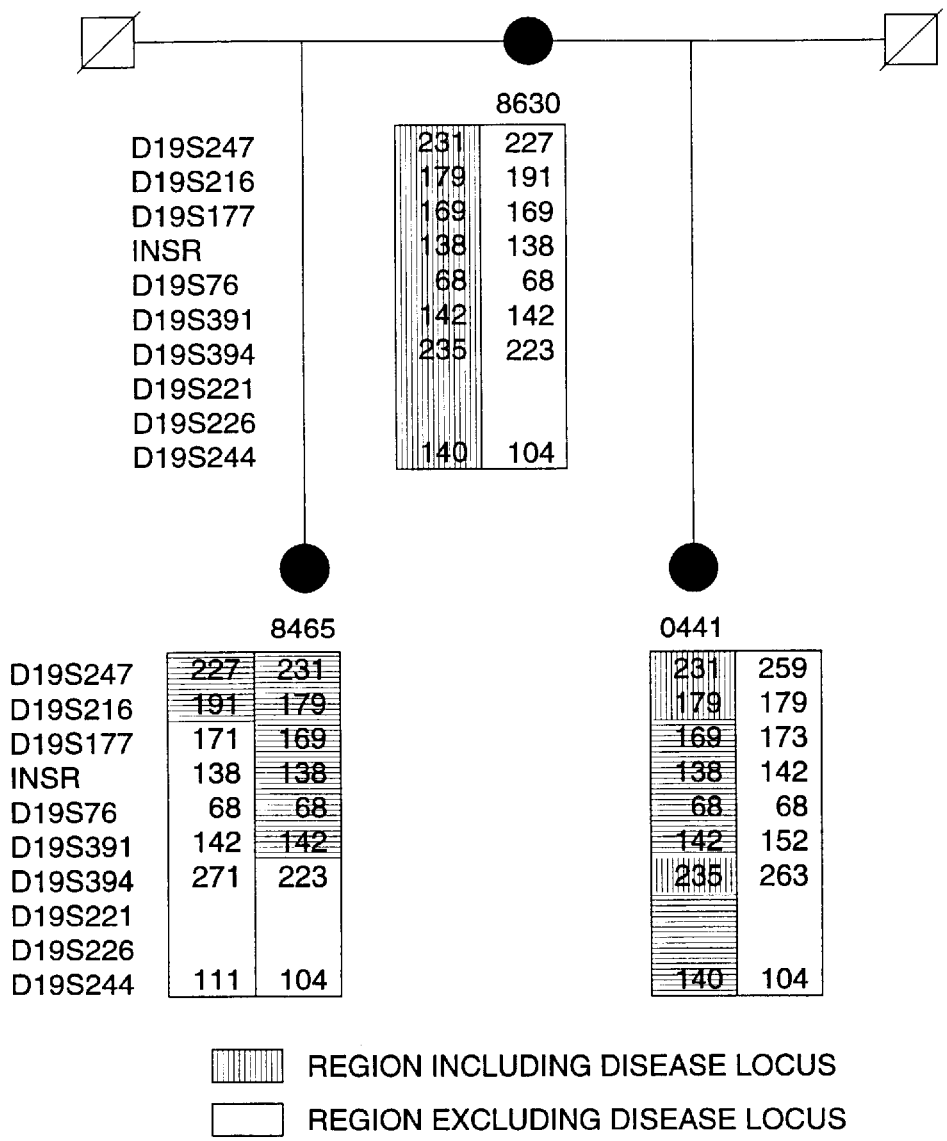
Figure 1F:
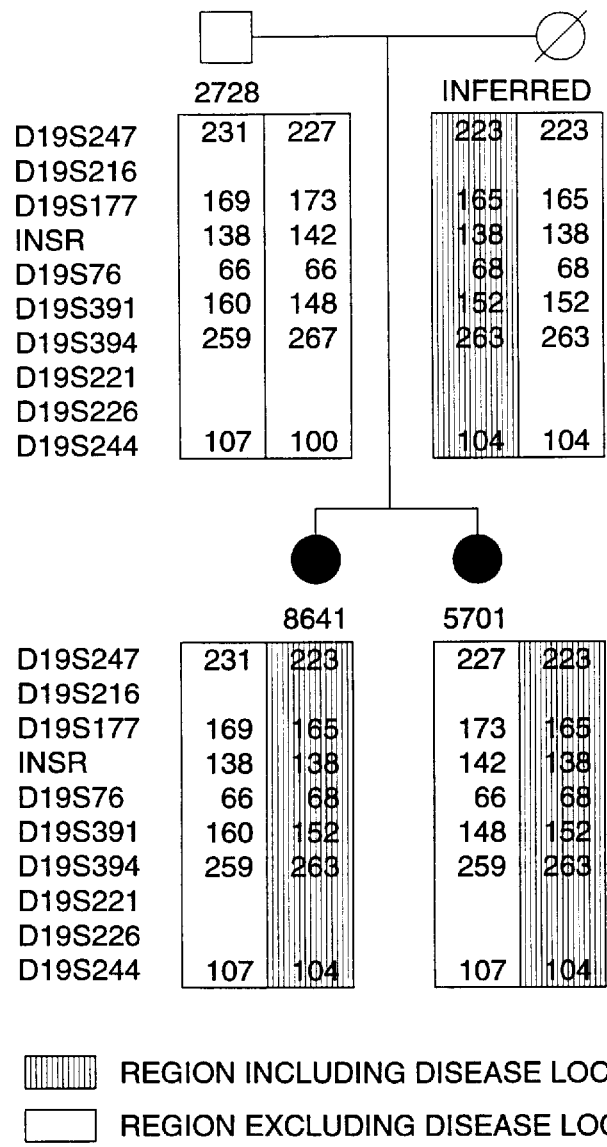

The term "corresponds to" is used herein to mean that a polynucleotide sequence is homologous to all or a portion of a reference polynucleotide sequence, or that a polypeptide sequence is identical to a reference polypeptide sequence. In contradistinction, the term "complementary to" is used herein to mean that the complementary sequences is homologous to all or a portion of a reference polynucleotide sequence. For illustration, the nucleotide sequence "TATAC" corresponds to a reference sequence "TATAC" and is complementary to a reference sequence "GTATA".

Hybridization probes may be DNA or RNA, or any synthetic nucleotide structure capable of binding in a base-specific manner to a complementary strand of nucleic acid. For example, probes include peptide nucleic acids, as described in Nielsen et al., *Science* 254:1497–1500 (1991).

"Linkage" describes the tendency of genes, alleles, loci or genetic markers to be inherited together as a result of their location on the same chromosome, and is measured by percent recombination between the two genes, alleles, loci or genetic markers. "Centimorgan" is a unit of genetic distance signifying linkage between two genetic markers, alleles, genes or loci, corresponding to a probability of recombination between the two markers or loci of 1% for any meiotic event. "Linkage disequilibrium" or "allelic association" means the preferential association of a particular allele, locus, gene or genetic marker with a specific allele, locus, gene or genetic marker at a nearby chromosomal location more frequently than expected by chance for any particular allele frequency in the population.

An "oligonucleotide" can be DNA or RNA, and single- or double-stranded. Oligonucleotides can be naturally occurring or synthetic, but are typically prepared by synthetic means.

"Polymorphic information content" is the sum of the frequency of each mating type multiplied by the probability that an offspring of that mating type being informative.

The term "primer" refers to an oligonucleotide capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligonucleotide. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term "primer" may refer to more than one primer, particularly in the case where there is some ambiguity in the information regarding one or both ends of the target region to be amplified. For instance, if a region shows significant levels of polymorphism or mutation in a population, mixtures of primers can be prepared that will amplify alternate sequences. A primer can be labeled, if desired, by incorporating a label detectable by spectroscopic, photochemical, biochemical, immunochemical, or chemical means. For example, useful labels include 32p, fluorescent dyes, electron-dense reagents, enzymes (as commonly used in an ELISA), biotin, or haptens and proteins for which antisera or monoclonal antibodies are available. A label can also be used to "capture" the primer, so as to facilitate the immobilization of either the primer or a primer extension product, such as amplified DNA, on a solid support. "Chromosome 19 set" means the two copies of chromosome 19 found in somatic cells or the one copy in germ line cells of a patient or family member. The two copies of chromosome 19 may be the same or different at any particular allele, including alleles at or near the depression locus. The chromosome 19 set may include portions of chromosome 19 collected in chromosome 19 libraries, such as plasmid, yeast, or phage libraries, as described in Sambrook et al., *Molecular Cloning*, 2nd Edition, and in Mandel et al., *Science* 258:103–108 (1992).

"Penetrance" is the percentage of individuals with a defective gene who show some symptoms of a trait resulting from that defect. Expressivity refers to the degree of expression of the trait (e.g., mild, moderate or severe).

"Polymorphism" refers to the occurrence of two or more genetically determined alternative sequences or alleles in a population. A polymorphic marker is the locus at which divergence occurs. Preferred markers have at least two alleles, each occurring at frequency of greater than 1%. A polymorphic locus may be as small as one base pair. Polymorphic markers suitable for use in the invention include restriction fragment length polymorphisms, variable number of tandem repeats (VNTR's), hypervariable regions, minisatellites, dinucleotide repeats and tetranucleotide repeats.

"Restriction fragment length polymorphism" (RFLP) means a variation in DNA sequence that alters the length of a restriction fragment as described in Botstein et al., *Am. J. Hum. Genet.* 32:314–331 (1980). The restriction fragment length polymorphism may create or delete a restriction site, thus changing the length of the restriction fragment. For example, the DNA sequence GAATTC are the six bases, together with its complementary strand CTTAAG which comprises the recognition and cleavage site of the restriction enzyme EcoRI. Replacement of any of the six nucleotides on either strand of DNA to a different nucleotide destroys the EcoRI site. This RFLP can be detected by, for example, amplification of a target sequence including the polymorphism, digestion of the amplified sequence with EcoRI, and size fractionation of the reaction products on an agarose or acrylamide gel. If the only EcoRI restriction enzyme site within the amplified sequence is the polymorphic site, the target sequences comprising the restriction site will show two fragments of predetermined size, based on the length of the amplified sequence. Target sequences without the restriction enzyme site will only show one fragment, of the length of the amplified sequence.

Similarly, the RFLP can be detected by probing an EcoRI digest of Southern blotted DNA with a probe from a nearby region such that the presence or absence of the appropriately sized EcoRI fragment may be observed. RFLP's may be caused by point mutations which create or destroy a restriction enzyme site, VNTR's, dinucleotide repeats, deletions, duplications, or any other sequence-based variation that creates or deletes a restriction enzyme site, or alters the size of a restriction fragment.

"Variable number of tandem repeats" (VNTR's) are short sequences of nucleic acids arranged in a head to tail fashion in a tandem array, and found in each individual, as described in Wyman et al., *Proc. Nat. Acad. Sci.* 77:6754–6758 (1980). Generally, the VNTR sequences are comprised of a core sequence of at least 16 base pairs, with a variable number of repeats of that sequence. Additionally, there may be variation within the core sequence, Jefferys et al., *Nature* 314:67–72 (1985). These sequences are highly individual, and perhaps unique to each individual. Thus, VNTR's may generate restriction fragment length polymorphisms, and may additionally serve as size-based amplification product differentiation markers.

"Dinucleotide repeats" comprise segments of at least about 10 base pairs of DNA consisting of a variable number of CA tandem repeats. The dinucleotide repeats are a subclass of all short tandem repeat sequences, Clemens et al., *Am. J. Hum. Genet.* 49:951–960 (1991). The dinucleotide repeats are generally spread throughout the chromosomal DNA of an individual. The number of CA dinucleotides in any particular tandem array varies greatly from individual to individual, and thus, dinucleotide repeats may serve to generate restriction fragment length polymorphisms, and may additionally serve as size-based amplification product differentiation markers.

DETAILED DESCRIPTION

I. Methods of Diagnosing Depression

The invention provides methods of identifying patients having a variant allele of a gene associated with a phenotype of depression. The gene (dep) is located in human chromosome 19 in the region conventionally designated p13 by reference to cytological markers and DNA. See *Cytogenet& Cell Genet.* 60:87–95 (1992); Franke, *Cytogenet. Cell. Genet.* 65:206–219 (1994); ISCN (1985); Weissenbach et al., *Nature* 359:794 (1992); Gyapay et al., *Nature Genetics* 7:246 (1994); Murray, CHLC Report (1994). Specifically, the gene is within a segment of about 30 cM between polymorphic markers D19S247 and D19S244. An allele of the gene present in persons not suffering from depression is arbitrarily designated as wildtype. A variant allele of the gene is associated with a phenotype of depression in that an addition, deletion or substitution of nucleotides relative to the wildtype allele causes a phenotype of depression, as defined by the Diagnostic and Statistical Manual (DSM)-IV criteria (see Example 1) in at least some individuals bearing the variant allele. The phenotype may result from a nucleotide change in the gene (addition, deletion or substitution) affecting expression of the gene by altering the kinetics of expression or the nature of the resulting expression product. For example, some changes reduce transcription or translation of an expression product. Other changes result in a polypeptide having altered properties (cf. the sickle cell mutation). Still other changes introduce a premature stop codon thereby resulting in truncated expression product.

A substantial proportion of patients having a variant copy of dep experience symptoms of depression, although it is often not evident from those symptoms alone, that the phenotypic complaints should properly be classified as depression. The present genetic tests provide more accurate means for diagnosing depression. Physicians informed of the correct diagnosis can ensure that patients receive prophylactic or therapeutic treatment appropriate to the genetic and biochemical bases.

The methods are also useful for in utero screening of fetuses for the presence of a variant dep allele. Identification of such variations offers the possibility of gene therapy. For couples known to be at risk of giving rise to affected progeny, diagnosis can be combined with in vitro reproduction procedures to identify an embryo having wildtype dep alleles before implantation. Screening children shortly after birth is also of value in identifying those having the variant gene. Early detection allows administration of appropriate treatment.

A. Mode of Inheritance

Example 4 presents evidence that a genetic subtype of depression can be inherited in an autosomal dominant fashion. This subtype is characterized by co-morbidity with migraine with aura. The subtype is manifested as a number of recognized subtypes of depression including major depressive disorders. The autosomal dominant mode of inheritance is unexpected in view of prior reports that depression is about twice as prevalent in females than males. The autosomal dominant mode of inheritance results in equal prevalence of the disease gene in males and females. However, penetrance variations between males and females could explain the difference in phenotypic rates.

This recognition is of immediate benefit in diagnosing an asymptomatic patient with a relative suffering from depression in a family, some of whose members have a genetic subtype of depression associated with the dep gene. It is apparent that the patient is also at risk of having acquired the variant allele associated with the disease, and subsequently developing symptoms of the disease. For example, if the patient has a parent suffering from depression, the odds of the patient having acquired the variant allele are 50%. The odds of the patient actually developing the disease are probably somewhat less than 50% because of incomplete penetrance of the disease. For example, at a penetrance of 70%, the odds of the patient acquiring the disease would be 35%.

B. Diagnosis from Linked Polymorphic Markers

The invention further provides methods of diagnosing susceptibility to depression by detection of polymorphic markers linked to the dep gene on human chromosome 19. Markers are linked if they occur within 50 cM from each other or the dep gene. Preferably, markers occur within 15 cM and more preferably within 5 or 1 cM of the gene. The closer the polymorphic marker is to dep locus, the less likely there is to be physical recombination between the two loci at meiosis. The polymorphic marker is usually outside the dep gene, but may also occur within the gene. The human chromosomes are subdivided into regions by cytological and polymorphic markers. Example 4 shows that preferred markers include those mapped between D19S216 and D19S244, including INSR, D19S391 and D19S394. Publications providing a detailed description of these and other polymorphic markers from the p13 region of chromosome 19 are provided in Table 3 and incorporated by reference in their entirety for all purposes. D19S391 shows the strongest linkage of markers tested to date. Thus, this marker and other markers within about 5 cM of it are preferred. Ideally, markers occur within the dep gene itself.

The methods determine which alleles of a linked polymorphic marker are present in the patient being diagnosed. For example, if the polymorphic marker is an RFLP, the alleles differ in the size of a restriction fragment. The determination is typically made by PCR amplification of a segment spanning the polymorphism and gel analysis of the amplification product. If one of the alleles present in the patient is known to be in phase with a variant dep locus (i.e., present on the same chromosome), it is concluded with a high probability that the patient has a variant dep gene and is susceptible to developing depression. The closer linked the polymorphic marker to dep, the higher the probability that the patient has received the variant dep gene. See Sutherland & Mulley, *Clinical Genetics* 37:2–11 (1990). Preferably, the methods analyze the presence of alleles of two polymorphic markers spaced either side of the dep gene and both in phase with the gene. Absent a rare double recombination event, the presence of both alleles signals the presence of the variant gene.

The above method requires knowledge that a particular allele of a marker is in phase with the variant form of the dep gene. This information is acquired from analyzing the phenotype and polymorphic content of relatives of the patient in a family, some of whose members exhibit the genetic subtype of depression associated with comorbidity with migraine with aura. The linkage and/or phase determinations are usually performed before analysis of DNA from the patient.

Linkage can be established by any of the methods discussed in Example 4. Determinations of linkage and/or phase are usually performed before analysis of DNA from the patient. A phase determination requires at least two relatives of the patient who are of known phenotype for depression, at least one of the relatives having the disease and being heterozygous for the marker. In practice, a relative having the disease is screened at several polymorphic markers to identify at least one marker in which the relative is heterozygous. The phase of this marker is then set by determining which alleles of the marker are present in a second relative of known phenotype. Strategies for setting phase in different families are describe by Lazarou, *Clinical Genetics* 43:150–156 (1993). For example, consider two relatives, X (with disease) having alleles 101 and 102 of a marker linked to the disease, and Y (without disease) being homozygous for allele 101. It can be concluded that in this family, the 102 allele is in phase with the variant dep gene. As a further example, consider X (with disease) having alleles 101 and 102 and Y (with disease) having alleles 101 and 103. It is deduced that the 101 allele is in phase with the variant gene. Within a family, the allele of a closely linked marker that is in phase with the variant gene is usually the same in each affected family member because there is a low probability of recombination between the two loci. The more closely related the relatives to the patient, the more likely phase is to be conserved between the relatives and the patient. Thus, it is preferred that one of the relatives used in setting phase is a parent of the patient. Once phase has been determined for a family, multiple members of the family can be diagnosed without repeating the analysis. In general, the phase relationship between an allele of a polymorphic marker and a variant allele of the dep gene is different in each family. However, certain alleles may be in linkage disequilibrium with the dep gene. For such markers, the same allele is likely to be in phase with the variant allele of the dep gene in any family. Thus, once such an allele is identified it is not necessary to set phase in every family to be tested.

C. Direct Assays for dep Gene

Having localized the dep gene as described infra, variations can be detected by more direct methods. These methods represent a special case of the methods described above in which the polymorphic marker being detected is a variation arising within the dep gene.

1. Detection of Uncharacterized Variations

Hitherto uncharacterized variations in the dep gene are identified and localized to specific nucleotides by comparison of nucleic acids from an individual with depression with an unaffected individual, preferably a relative of the affected individual. Comparison with a relative is preferred because the possibility of other polymorphic differences between the patient and person being compared, not related to the depression phenotype, is lower. Various screening methods are suitable for the comparison including ribonuclease cleavage, denaturing gradient-gel electrophoresis, carbodiimide modification, chemical cleavage of mismatch, heteroduplex analysis and direct sequencing. See Cotton, *Mutation Res.* 285:125–144 (1993). Comparison can be initiated at either cDNA or genomic level. Initial comparison is often easier at the cDNA level because of its shorter size. Corresponding genomic changes are then identified by amplifying and sequencing a segment from the genomic exon including the site of change in the cDNA. In some instances, there is a simple relationship between genomic and cDNA changes. That is, a single base change in a coding region of genomic DNA gives rise to a corresponding changed codon in the cDNA. In other instances, the relationship between genomic and cDNA changes is more complex. Thus, for example, a single base change in genomic DNA creating an aberrant splice site can give rise to deletion of a substantial segment of cDNA.

2. Detection of Characterized Changes

The preceding methods serve to identify particular changes responsible for depression. In any particular family, it is likely that all affected members have the same change. Individuals from different families may or may not have the same change. However, typically, many individuals have one of a relatively small number of changes. By analogy, in cystic fibrosis, about seventy percent of individuals have the same mutation in the CFTR gene. Once a change has been identified within a family, and/or as occurring within a population of affected individuals at a significant frequency, individuals can be tested for that change by various methods. These methods include allele-specific oligonucleotide hybridization, allele-specific amplification, ligation, primer extension and artificial introduction of extension sites (see Cotton, supra). For example, the allele-specific detection method uses one oligonucleotide exhibiting a perfect match to a target segment of the dep gene having the change and a paired probe exhibiting a perfect match to the corresponding wildtype segment. If the individual is homozygous wildtype, only the wildtype probe binds. If the individual is a heterozygous variant, both probes binds. If the individual is a homozygous variant (rare), only the variant probe binds. Paired probes for several variations can be immobilized as an array and the presence of several variations can thereby be analyzed simultaneously. Of course, the methods noted above, for analyzing uncharacterized variations can also be used for detecting characterized variations.

II. Identification of the dep Gene

The invention further provides methods of screening for the dep gene. In these methods, the position of the dep gene is localized by determining LOD scores for different markers on chromosome 19 between positions D19S247 and D19S244. The strategy underlying these methods is to select successive markers progressively closer to the gene, each marker being chosen based on the linkage distance established for a previous marker. Linkage distance is the distance from a marker at which the LOD score of the marker from the dep gene is maximized. For example, if a first polymorphic marker gives a maximum LOD score at a linkage distance of 5 cM, one would then select a second polymorphic marker within a 10 cM segment centered about the first polymorphic marker. The linkage distance of the second polymorphic marker to the gene is then determined. If this linkage distance is less than that of the first polymorphic marker, one then selects a further polymorphic marker within the linkage distance of the second polymorphic marker. If the linkage distance of the second polymorphic marker is greater than that of the first polymorphic marker, one then selects a further polymorphic marker within the linkage distance of the first polymorphic marker, on the side distal from the second polymorphic marker. By continually identifying polymorphic markers progressively closer to the gene, it is possible to localize the position of the gene to a relatively small segment of DNA (e.g., about 1, 2 or 3 Mb) for which more detailed molecular studies are feasible.

The position of the dep gene can also be localized by haplotype analysis as described in Example 4. See also *Current Protocols in Human Genetics* (eds. Dracopli et al., Wiley, 1994), Unit 1.3 (incorporated by reference in its entirety for all purposes). In this analysis, the phenotype with respect to depression is determined for successive generations of family members. Family members are then tested to determine which alleles are present for polymorphic markers mapping close to the dep gene (i.e., between D19S247 and D19S244). The alleles present are assigned to one of the two copies of chromosome 19 present in the individual whereby the number of recombination events between successive generations of the family is minimized. This analysis reveals which of the two copies of chromosome 19 an individual has received from each parent, and where, if at all, a recombination event has occurred in this chromosome in the region of interest. By identifying a site of recombination between members of successive generations in a family, and knowing whether the members share or differ in the depression phenotype, the location of the dep gene relative to the site of recombination (i.e., on one side or the other) is revealed. The dep gene is described as "proximal" to the site of recombination (or a marker bordering the site of recombination), if the gene occurs between the site of recombination (or the marker) and the centromere. The dep gene is described as "distal" to the site of recombination (or the marker), if the gene occurs between the site of recombination (or the marker) and the telomere. The site of recombination can vary between different generations and between different families. Thus, the possible positions in which the dep gene can occur consistent with its proximal or distal nature with respect to each point of recombination identified is progressively confined as more families are tested.

Having localized the dep gene to a small segment within the p13 region of chromosome 19, the region can be mapped for restriction sites by pulse gel electrophoresis. A library is then prepared and enriched for clones mapping to this region. Chromosomal segments are preferably cloned into YAC vectors.

Such vectors offer a capacity of 100–1000 kb per vector. See Burke et al., *Science* 236:806–812 (1987); Traver et al., *Proc. Natl. Acad. Sci. USA* 86:5898–5902 (1989); McCormick et al., *Proc. Natl. Acad. Sci USA* 86:9991–9995 (1989). Thus, only a few clones are required to cover the entire segment to which the dep gene has been localized. As a starting material for preparing such a library, a library of the whole of human chromosome 19 is already available. See Davies & Read, *Molecular Basis of Inherited Disease* (2nd ed. 1992). Clones mapping to the region of interest can be isolated by, e.g., chromosome walking. Briefly, a first marker bordering the segment of interest is used as a probe to identify a first clone containing sequence complementary to the probe. A second probe is then designed based on the sequence of the first clone at the end nearest the dep gene. The second probe is then used to isolate a second clone, which is in turn used to design a third probe. The process continues until a clone is isolated which hybridizes to a second marker, known to be on the distal side of the dep gene from the first marker. See Wainwright, *Med. J. Australia* 159:170–174 (1993); DOE, *Primer On Molecular Genetics* (Washington DC, June 1992); Collins, *Nature Genetics* 1:3–6 (1992) (each of which is incorporated by reference in its entirety for all purposes). So-called jumping libraries can also be prepared covering separated portions of the segment of interest. See Davies, supra.

Preferably, a small library of clones completely spanning the region of interest is obtained, which is substantially free (at least 75% free) of clones having segments mapping elsewhere in chromosome 19. The region of interest is bordered by D19S247 and D19S244, and ~5 Mb segments spanning D19S391 are of particular interest. Typically, a library spanning 1 Mb of human DNA contains 1–10 genes. The clones are sequenced to search for open-reading frames and analyzed for transcription by Northern blotting, in situ hybridization, zoo-blotting (probing with xenogeneic DNA to identify conserved sequences), exon trapping (Davies, supra) and/or HTF-island mapping (CCGG sites associated with the 5' end of many genes). Having identified an open reading frame that appears to be expressed, this region of DNA is compared between affected and unaffected members of a family to identify the presence of variations that correlate with the disease phenotype.

III. Expression Systems

Identification of the dep gene permits the production of the gene product. The cDNA fragment or any other nucleic acid encoding the dep gene can be used to make an expression construct for the dep gene. The expression construct typically comprises one or more nucleic acid sequences encoding the dep gene operably linked to a native or other promoter. Usually, the promoter is a eukaryotic promoter for expression in a mammalian cell. The transcription regulation sequences typically include a heterologous enhancer or promoter which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the dep gene, both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof. Preferred host cells are able to process the dep gene product to produce an appropriate mature polypeptide. Processing includes glycosylation, ubiquitination, disulfide bond formation, general post-translational modification, and the like.

The protein may be isolated by conventional means of protein biochemistry and purification to obtain a substantially pure product, i.e., 80, 95 or 99% free of cell component contaminants, as described in Jacoby, *Methods in Enzymology* Volume 104, Academic Press, New York (1984); Scopes, *Protein Purification, Principles and Practice,* 2nd Edition, Springer-Verlag, New York (1987); and Deutscher (ed), *Guide to Protein Purification, Methods in Enzymology,* Vol. 182 (1990). If the protein is secreted, it can be isolated from the supernatant in which the host cell is grown. If not secreted, the protein can be isolated from a lysate of the host cells.

The invention further provides transgenic nonhuman animals capable of expressing an exogenous dep gene and/or having one or both alleles of an endogenous dep gene inactivated. Expression of an exogenous dep gene is usually achieved by operably linking the gene to a promoter and optionally an enhancer, and microinjecting the construct into a zygote. See Hogan et al., "Manipulating the Mouse Embryo, A Laboratory Manual," Cold Spring Harbor Laboratory. Inactivation of endogenous dep genes can be achieved by forming a transgene in which a cloned dep gene is inactivated by insertion of a positive selection marker. See Capecchi, *Science* 244:1288–1292 (1989). The transgene is then introduced into an embryonic stem cell, where it undergoes homologous recombination with an endogenous dep gene. Mice and other rodents are preferred animals. Such animal provide useful drug screening systems.

In addition to substantially full-length polypeptides expressed by the dep gene, the present invention includes biologically active fragments of the polypeptides, or analogs thereof, including organic molecules which simulate the interactions of the peptides. Biologically active fragments include any portion of the full-length polypeptide which confers a biological function on the dep gene product, including ligand binding, substrate for other molecules, dimer association, and the like. Ligand binding includes binding by nucleic acids, proteins or polypeptides, small biologically active molecules, or large cellular structures.

Polyclonal and/or monoclonal antibodies to the dep gene product are also provided. Antibodies can be made by injecting mice or other animals with the dep gene product or synthetic peptide fragments thereof. Monoclonal antibodies are screened by methods known in the art, as are described, for example, in Harlow & Lane, *Antibodies, A Laboratory Manual,* Cold Spring Harbor Press, New York (1988), and Goding, *Monoclonal antibodies, Principles and Practice* (2d ed.) Academic Press, New York (1986). Monoclonal antibodies are tested for specific immunoreactivity with an epitope of the dep gene product. These antibodies are useful in diagnostic assays for detection of the dep gene product or a variant form thereof, or as an active ingredient in a pharmaceutical composition.

IV. Methods of Treatment

There are a number of drugs presently in use for treating depression. However, no clear distinctions have been drawn between depression patients in prescribing decisions. The present discovery that at least some subtypes of depression are associated with a common genetic and presumably, biochemical bases allows drug screening programs to be conducts in a group of patients having homogeneous disposition with respect to the dep gene. Such a groups is identified by the diagnostic methods discussed above.

The provision of DNA encoding the dep gene is also useful in developing new drugs and methods of treatment for depression. For example, variations in the dep gene, including regulatory sequences, can be corrected by gene therapy. See Rosenberg, *J. Clin. Oncol.* 10:180–199 (1992). Gene therapy is preferably performed in utero rather than after birth, because of the undifferentiated nature of cells in a developing fetus. Exogenously supplied corrective genes integrate into the genomes of undifferentiated cells, and are subsequently distributed and expressed in entire tissues by the proliferation and differentiation of the ancestor cell.

The provision of the dep gene product also allows screening for a receptor or soluble molecules that interact with the same and design of agents that agonize or antagonize this interaction. Such agents include monoclonal antibodies against the dep gene product, fragments of the dep gene product that compete with the full-length protein for binding, and synthetic peptides or analogs thereof selected from random combinatorial libraries. See, e.g., Ladner et al., U.S. Pat. No. 5,223,409 (1993) (incorporated by reference in its entirety for all purposes). Therapeutic agents also includes transcription factors, and the like, which stimulate expression of the dep gene.

V. Diagnostic Kits

The present invention also includes kits for the practice of the methods of the invention. The kits comprise a vial, tube, or any other container which contains one or more oligonucleotides, which hybridizes to a DNA segment within chromosome 19p13, which DNA segment is linked to the dep gene. Preferably, the oligonucleotide hybridizes to a segment of chromosome 19 between markers D19S247 and D19S244. Some kits contain two such oligonucleotides, which serve as primers to amplify a segment of chromosome DNA. The segment selected for amplification can be a polymorphic marker linked to the dep gene or a region from the dep gene that includes a site at which a variation is known to occur. Some kits contain a pair of oligonucleotides for detecting precharacterized variations. For example, some kits contain oligonucleotides suitable for allele-specific oligonucleotide hybridization, or allele-specific amplification hybridization. The kits may also contain components of the amplification system, including PCR reaction materials such as buffers and a thermostable polymerase. In other embodiments, the kit of the present invention can be used in conjunction with commercially available amplification kits, such as may be obtained from GIBCO BRL (Gaithersburg, Md.) Stratagene (La Jolla, Calif.), Invitrogen (San Diego, Calif.), Schleicher & Schuell (Keene, N.H.), Boehringer Mannheim (Indianapolis, Ind.). The kits can also include positive or negative control reactions or markers, molecular weight size markers for gel electrophoresis, and the like. The kits usually include labelling or instructions indicating the suitability of the kits for diagnosing depression and indicating how the oligonucleotides are to be used for that purpose. The term "label" is used generically to encompass any written or recorded material that is attached to, or otherwise accompanies the diagnostic at any time during its manufacture, transport, sale or use.

MODES OF PRACTICING THE INVENTION

1. Linkage Analysis

Determining linkage between a polymorphic marker and a locus associated with a particular phenotype is performed by mapping polymorphic markers by observing whether they co-segregate with the depression phenotype on a chromosome in an informative meiosis. See, e.g., Kerem et al., *Science* 245:1073–1080 (1989); Monaco et al., *Nature* 316:842 (1985); Yamoka et al., *Neurology* 40:222–226 (1990), and as reviewed in Rossiter et al., *FASEB Journal* 5:21–27 (1991). A single pedigree rarely contains enough informative meioses to provide definitive linkage, because families are often small and markers may be not sufficiently informative. For example, a marker may not be polymorphic in a particular family.

Linkage may be established by an affected sib-pairs analysis as described in Terwilliger & Ott, *Handbook of Human Genetic Linkage* (Johns Hopkins, Md., 1994), Ch. 26. This approach requires no assumptions to be made concerning penetrance or variant frequency, but only takes into account the data of a relatively small proportion (i.e., the SIB pairs) of all the family members whose phenotype and polymorphic markers have been determined. Specifically, the affected SIB pairs analysis scores each pair of affected SIBS as sharing (concordant) or not sharing (discordant) the same allelic variant of each polymorphic marker. For each marker, a probability is then calculated that the observed ratio of concordant to discordant SIB pairs would arise without linkage of the marker.

As described in Thompson & Thompson, *Genetics in Medicine*, 5th ed, 1991, W.B. Saunders Company, Philadelphia, in linkage analysis, one calculates a series of likelihood ratios (relative odds) at various possible values of θ, ranging from θ=0.0 (no recombination) to θ=0.50 (random assortment). Thus, the likelihood at a given value of θ

$$= \frac{\text{likelihood of data if loci linked at } \theta}{\text{likelihood of data if loci unlinked}}$$

The computed likelihoods are usually expressed as the $\log_{10}$ of this ratio and called a "lod score" for "logarithm of the odds." For example, a lod score of 5 indicates 100,000,1 odds that the linkage being observed did not occur by chance.

The use of logarithms allows data collected from different families to be combined by simple addition. Computer programs are available for the calculation of lod scores for differing values of θ. Available programs include LIPED, and MLINK (Lathrop, *Proc. Nat. Acad. Sci.* 81:3443–3446 (1984).

For any particular lod score, a recombination fraction may be determined from mathematical tables. See Smith et al., *Mathematical tables for research workers in human genetics* (Churchill, London, 1961) and Smith, *Ann. Hum. Genet.* 32:127–150 (1968). The value of θ at which the lod score is the highest is considered to be the best estimate of the recombination fraction, the "maximum likelihood estimate".

Positive lod score values suggest that the two loci are linked, whereas negative values suggest that linkage is less likely (at that value of θ) than the possibility that the two loci are unlinked. Positive lod scores are considered evidence that the two loci being compared are linked. By convention, a combined lod score of +3 or greater (equivalent to greater than 1000,1 odds in favor of linkage) is considered definitive evidence that two loci are linked. Similarly, by convention, a negative lod score of −2 or less is taken as definitive evidence against linkage of the two loci being compared. If there are sufficient negative linkage data, a locus can be excluded from an entire chromosome, or a portion thereof, a process referred to as exclusion mapping. The search is then focussed on the remaining non-excluded chromosomal locations. For a general discussion of lod scores and linkage analysis, see, e.g., T. Strachan, Chapter 4, "Mapping the human genome" in *The Human Genome*, 1992 BIOS Scientific Publishers Ltd. Oxford.

The data can also be subjected to haplotype analysis. This analysis assigns allelic markers between the chromosomes of an individual such that the number of recombinational events needed to account for segregation between generations is minimized. Linkage may also be established by determining the relative likelihood of obtaining observed segregation data for any two markers when the two markers are located at a recombination fraction θ, versus the situation in which the two markers are not linked, and thus segregating independently.

2. Isolation and Amplification of DNA

Samples of patient, proband or family member genomic DNA is isolated from any convenient source including saliva, buccal cells, hair roots, blood, cord blood, amniotic fluid, interstitial fluid, peritoneal fluid, chorionic villus, and any other suitable cell or tissue sample with intact interphase nuclei or metaphase cells. The cells can be obtained from solid tissue as from a fresh or preserved organ or from a tissue sample or biopsy. The sample can contain compounds which are not naturally intermixed with the biological material such as preservatives, anticoagulants, buffers, fixatives, nutrients, antibiotics, or the like.

Methods for isolation of genomic DNA from these various sources are described in, for example, Kirby, *DNA Fingerprinting, An Introduction*, W.H. Freeman & Co. New York (1992). Genomic DNA can also be isolated from cultured primary or secondary cell cultures or from transformed cell lines derived from any of the aforementioned tissue samples.

Samples of patient, proband or family member RNA can also be used. RNA can be isolated from tissues expressing the dep gene as described in Sambrook et al., supra. RNA can be total cellular RNA, mRNA, poly A+ RNA, or any combination thereof. For best results, the RNA is purified, but can also be unpurified cytoplasmic RNA. RNA can be reverse transcribed to form DNA which is then used as the amplification template, such that the PCR indirectly amplifies a specific population of RNA transcripts. See, e.g., Sambrook, supra, Kawasaki et al., Chapter 8 in PCR Technology, (1992) supra, and Berg et al., *Hum. Genet.* 85:655–658 (1990).

PCR Amplification

The most common means for amplification is polymerase chain reaction (PCR), as described in U.S. Pat. Nos. 4,683,195, 4,683,202, 4,965,188 each of which is hereby incorporated by reference.

If PCR is used to amplify the target regions in blood cells, heparinized whole blood should be drawn in a sealed vacuum tube kept separated from other samples and handled with clean gloves. For best results, blood should be processed immediately after collection; if this is impossible, it should be kept in a sealed container at 4° C. until use. Cells in other physiological fluids may also be assayed. When using any of these fluids, the cells in the fluid should be separated from the fluid component by centrifugation.

Tissues should be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. One method of isolating target DNA is crude extraction which is useful for relatively large samples. Briefly, mononuclear cells from samples of blood, amniocytes from amniotic fluid, cultured chorionic villus cells, or the like are isolated by layering on sterile Ficoll-Hypaque gradient by standard procedures. Interphase cells are collected and washed three times in sterile phosphate buffered saline before DNA extraction. If testing DNA from peripheral blood lymphocytes, an osmotic shock (treatment of the pellet for 10 sec with distilled water) is suggested, followed by two additional washings if residual red blood cells are visible following the initial washes. This will prevent the inhibitory effect of the heme group carried by hemoglobin on the PCR reaction. If PCR testing is not performed immediately after sample collection, aliquots of $10^6$ cells can be pelleted in sterile Eppendorf tubes and the dry pellet frozen at −20° C. until use.

The cells are resuspended ($10^6$ nucleated cells per 100 μl) in a buffer of 50 mM Tris-HCl (pH 8.3), 50 mM KCl 1.5 mM $MgCl_2$, 0.5% Tween 20, 0.5% NP40 supplemented with 100 μg/ml of proteinase K. After incubating at 56° C. for 2 hr, the cells are heated to 95° C. for 10 min to inactivate the proteinase K and immediately moved to wet ice (snap-cool). If gross aggregates are present, another cycle of digestion in the same buffer should be undertaken. Ten μl of this extract is used for amplification.

When extracting DNA from tissues, e.g., chorionic villus cells or confluent cultured cells, the amount of the above mentioned buffer with proteinase K may vary according to the size of the tissue sample. The extract is incubated for 4–10 hrs at 50°–60° C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in *PCR Technology*, Ehrlich, H. A. (ed.), Stockton Press, New York, which is incorporated herein by reference. PCR can be employed to amplify target regions chromosome 19 in very small numbers of cells (1000–5000) derived from individual colonies from bone marrow and peripheral blood cultures. The cells in the sample are suspended in 20 μl of PCR lysis buffer (10 mM Tris-HCl (pH 8.3), 50 mM KCl, 2.5 mM $MgCl_2$, 0.1 mg/ml gelatin, 0.45% NP40, 0.45% Tween 20) and frozen until use. When PCR is to be performed, 0.6 μl of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., *Nucleic Acids Res.* 16:1215 (1988), which is incorporated herein by reference. Mononuclear cells are separated on a Ficoll-Hypaque gradient. The cells are resuspended in 3 ml of lysis buffer (10 mM Tris-HCl, 400 mM NaCl, 2 mM $Na_2EDTA$, pH 8.2). Fifty μl of a 20 mg/ml solution of proteinase K and 150 μl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 μl of the 20 mg/ml proteinase K solution is mixed in the solution and incubated for another night at 37° C. on a gently rocking or rotating platform. Following adequate digestion, one ml of a 6M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air dried. The precipitate is placed in distilled water and dissolved.

Kits for the extraction of high-molecular weight DNA for PCR include a Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, La Jolla, Calif.), TurboGen Isolation Kit (Invitrogen, San Diego, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm.

After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for an sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH-Quantitative Biology*, 43:63–67; and Radding, 1982, *Ann. Rev. Genetics* 16:405–436, each of which is incorporated herein by reference).

Template-dependent extension of primers in PCR is catalyzed by a polymerizing agent in the presence of adequate amounts of four deoxyribonucleotide triphosphates (typically DATP, dGTP, dCTP, and dTTP) in a reaction medium comprised of the appropriate salts, metal cations, and pH buffering system.

Suitable polymerizing agents are enzymes known to catalyze template-dependent DNA synthesis.

In some cases, the target regions may encode at least a portion of a protein expressed by the cell. In this instance, mRNA may be used for amplification of the target region. Alternatively, PCR can be used to generate a cDNA library from RNA for further amplification, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or *Thermus thermophilus* (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, *E. coli* DNA polymerase I or its Klenow fragment, $T_4$ DNA polymerase, Tth polymerase, and Taq polymerase, a heat-stable DNA polymerase isolated from *Thermus aquaticus* and commercially available from Perkin Elmer Cetus, Inc. The latter enzyme is widely used in the amplification and sequencing of nucleic acids. The reaction conditions for using Taq polymerase are known in the art and are described in Gelfand, 1989, *PCR Technology*, supra.

4. Allele Specific PCR

Allele-specific PCR differentiates between chromosome 19 target regions differing in the presence or absence of a variation or polymorphism. PCR amplification primers are chosen which bind only to certain alleles of the target sequence. Thus, for example, amplification products are generated from those chromosome 19 sets which contain the primer binding sequence, and no amplification products are generated in chromosome 19 sets without the primer binding sequence. This method is described by Gibbs, *Nucleic Acid Res.* 17:12427–2448 (1989).

5. Allele Specific Oligonucleotide Screening Methods

Further diagnostic screening methods employ the allele-specific oligonucleotide (ASO) screening methods, as described by Saiki et al., *Nature* 324:163–166 (1986). oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed that under low stringency will bind to both polymorphic forms of the allele, but that at higher stringency, will bind detectably more strongly to the allele to which they correspond. Stringency conditions can be devised in which an essentially binary response is obtained, i.e., an ASO corresponding to a variant form of the dep gene will hybridize to that allele, and not to the wildtype allele.

6. Ligase Mediated Allele Detection Method

Target regions of a patients can be compared with target regions in unaffected and affected family members by ligase-mediated allele detection. See Landegren et al., *Science* 241:1077–1080 (1988). Ligase may also be used to detect point mutations in the ligation amplification reaction described in Wu et al., *Genomics* 4:560–569 (1989). The ligation amplification reaction (LAR) utilizes amplification of specific DNA sequence using sequential rounds of template dependent ligation as described in Wu, supra, and Barany, *Proc. Nat. Acad. Sci.* 88:189–193 (1990).

7. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature (Tm). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., *PCR Technology, Principles and Applications for DNA Amplification,* W.H. Freeman and Co, New York (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., *Meth. Enzymol.* 155:501–527 (1986), and Myers et al., in *Genomic Analysis, A Practical Approach,* K. Davies Ed. IRL Press Limited, Oxford, pp. 95–139 (1988), the contents of which are hereby incorporated by reference. The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine. Preferably, the GC clamp is at least 30 bases long. This method is particularly suited to target sequences with high Tm's.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

8. Single-Strand Conformation Polymorphism Analysis

Target sequences or alleles at the dep locus can be differentiated using single-strand conformation polymorphism analysis, which identifies base differences by alteration in electrophoretic migration of single stranded PCR products, as described in Orita et al., *Proc. Nat. Acad. Sci.* 86:2766–2770 (1989). Amplified PCR products can be generated as described above, and heated or otherwise denatured, to form single stranded amplification products. Single-stranded nucleic acids may refold or form secondary structures which are partially dependent on the base sequence. Thus, electrophoretic mobility of single-stranded amplification products can detect base-sequence difference between alleles or target sequences.

9. Chemical or Enzymatic Cleavage of Mismatches

Differences between target sequences can also be detected by differential chemical cleavage of mismatched base pairs, as described in Grompe et al., *Am. J. Hum. Genet.* 48:212–222 (1991). In another method, differences between target sequences can be detected by enzymatic cleavage of mismatched base pairs, as described in Nelson et al., *Nature Genetics* 4:11–18 (1993). Briefly, genetic material from a patient and an affected family member may be used to generate mismatch free heterohybrid DNA duplexes. As used herein, "heterohybrid" means a DNA duplex strand comprising one strand of DNA from one person, usually the patient, and a second DNA strand from another person, usually an affected or unaffected family member. Positive selection for heterohybrids free of mismatches allows determination of small insertions, deletions or other polymorphisms that may be associated with headache.

10. Non-PCR Based DNA Diagnostics

The identification of a DNA sequence linked to dep can made without an amplification step, based on polymorphisms including restriction fragment length polymorphisms in a patient and a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labelled directly or indirectly, such that by assaying for the presence or absence of the probe, one can detect the presence or absence of the target sequence. Direct labelling methods include radioisotope labelling, such as with 32P or 35S. Indirect labelling methods include fluorescent tags, biotin complexes which may be bound to avidin or streptavidin, or peptide or protein tags. Visual detection methods include photoluminescents, Texas red, rhodamine and its derivatives, red leuco dye and 3, 3', 5, 5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to the 19p13 region of chromosome 19, and thus defining a genetic marker linked to dep, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the p13 region of chromosome 19. Other suitable probes include portions of introns or intron/exon spanning regions from genomic fragments of chromosome 19, or portions of spacer DNA, i.e., DNA between genes that is not intronic.

Preferred tandem repeat hybridization probes for use according to the present invention are those that recognize a small number of fragments at a specific locus at high stringency hybridization conditions, or that recognize a larger number of fragments at that locus when the stringency conditions are lowered.

EXPERIMENTAL EXAMPLES

Example 1
Mode of Inheritance of Depression

Previous studies have reported that the ratio of female to male suffers is about 2:1 for depression. However, many of the studies from which these data were compiled failed to meet rigorous standards for genetic analysis. For example, most published family studies of depression have not interviewed all family members, relying instead on the diagnostic impression of the proband. Interviewing a proband on the nature, type and frequency of depression experienced by a parent or sibling is inherently untrustworthy. For example, it depends on the accuracy of the prior diagnosis (if any) of the family member. More significantly, it also depends on an accurate reporting of the symptoms, diagnosis and treatment of the depression from the family member to the proband. This accurate reporting may not occur for many personal or societal reasons. As a result, there is a significant under-reporting or mis-reporting of depression in first degree relatives where family members are not interviewed. Moreover, few studies have utilized the currently accepted DSM-IV criteria described below.

The DSM-IV criteria for depression are summarized in Table 1. The Clinical Rating Scale for Depression is provided in Table 2.

TABLE 1

MAJOR DEPRESSIVE DISORDER: DSM-IV DIAGNOSTIC CRITERIA
At least five of the following symptoms are present during the same period. At least (1.) depressed mood or (2.) loss of interest or pleasure must be present. Symptoms are present most of the day, nearly daily for at least 2 weeks.

1. Depressed mood (sometimes irritability in children and adolescents) most of the day, nearly every day
2. Markedly diminished interest or pleasure in almost all activities most of the day, nearly every day (as indicated either by subjective account or observation by others of apathy most of the time)
3. Significant weight loss/gain TABLE 1-continued MAJOR DEPRESSIVE DISORDER: DSM-IV DIAGNOSTIC CRITERIA
At least five of the following symptoms are present during the same period. At least (1.) depressed mood or (2.) loss of interest or pleasure must be present. Symptoms are present most of the day, nearly daily for at least 2 weeks.

4. Insomnia/hypersomnia
5. Psychomotor agitation/retardation
6. Fatigue (loss of energy)
7. Feelings of worthlessness (guilt)
8. Impaired concentration (indecisiveness)
9. Recurrent thoughts of death or suicide

TABLE 2

CLINICAL RATING SCALE FOR DEPRESSION

| | |
|---|---|
| None | Score = 0 |
| Meets no DSM criteria for a depressive disorder (Major depression, Dysthymia or Brief Recurrent Depression) Has never sought help for depressive sx Has never taken prescription meds for depressive sx | |
| Possible | Score = 1 |
| May have some depressive sx Family members may report depressive sx Does not meet DSM criteria for a depressive disorder Has never sought help Has never taken prescription medications for depression | |
| Mild | Score = 2 |
| May meet DSM criteria for a depressive disorder May have sought help Has never taken prescription medications for depression Depressive symptoms were transient | |
| Moderate | Score = 3 |
| Meets DSM criteria May have sought help May have taken prescription medications for depression Depressive episodes were transient but recurrent | |
| Severe | Score = 4 |
| Meets DSM criteria Has sought help Has usually taken prescription medications for depression Depressive episodes have been multiple throughout life If <20 years old, depression started by age 12 | |
| Severe and chronic | Score = 5 |
| Meets all criteria for "Severe" Has been diagnosed with depression Depressive episodes have been chronic throughout life | |

Persons enrolling in the present study and their families were screened for depression according to the DSM-IV criteria by administering the questionnaire provided in Appendix A. Persons enrolling in the study had been previously diagnosed as having a variant gene associated with migraine with aura (see copending application U.S. Ser. No. 08/366,288). The study therefore sought to identify linkage in a genetic subtype of depression exhibiting comorbidity with migraine with aura. Note that the DSM-IV provides conservative criteria for diagnosing patients with depression, and it is possible that some patients not meeting all requisite DSM-IV criteria would be diagnosed with depression by a physician and might indeed be suffering from depression. The rigorous application of DSM-IV criteria combined with exclusion of families where satisfaction of DSM-IV criteria is only marginal serves to exclude false positives from the analysis.

The probands were then interviewed directly by a physician for the possible presence of a depressive disorder. The physician was blinded to all genotype data.

The analysis identified ten probands having depression and for whom both parents were available and for whom at least one sibling and/or one parent and at least one child also had a history of clinical depression. All available first degree relatives (parents, siblings and children) above the age of 10 were interviewed using the same questionnaire as for the proband. Children under 10 were excluded due to their incomplete perception of and difficulty in accurately articulating the depression symptoms. Phenotypes were assigned to relatives by the same criteria as for the proband.

For each member of the families, genomic DNA was prepared and analyzed as described in Examples 2 and 3 for at least the following markers, D19S247, D19S216, INSR, D19S391, D19S76, D19S394, D19S244.

Example 2
Preparation of Genomic DNA

About 10 ml of blood was collected from each proband or family member into a tube containing $K_2$-EDTA or other anticoagulant. Red blood cells were lysed by addition of 4 volumes of 155 mM $NH_4CL$, 10 mM $KHCO_3$, and 0.1 mM EDTA-$Na_2$. After mixing and incubation at room temperature for 20 minutes, the white blood cells were pelleted by centrifugation. The lysis and centrifugation was repeated, and the final white cell pellet resuspended in 1 ml of phosphate buffered saline followed by 5 ml of SE buffer (75 mM NaCl, 25 mM EDTA, pH 8.00). Sodium dodecyl sulphate was added to 1%, and proteinase K to a final concentration of 200 μg/ml. The lysate was incubated at 55° C. for 24 to 48 hours. After digestion was completed, a prewarmed NaCl solution was added to a final concentration of 1.5M. An equal volume of chloroform was added, and the mixture extracted for one hour on a rocker platform at room temperature. The two phases were separated by centrifugation and the aqueous phase containing the DNA transferred to a clean tube. DNA was precipitated by addition of an equal volume of isopropanol and pelleted by centrifugation. The DNA pellet was washed with 70% ethanol, air dried and resuspended in 0.5 ml of 50 mM Tris HCl and 10 mM EDTA (pH 8.0). The concentration of the DNA was determined by absorbance at 260 nm. Diluted solutions at 20 ng per μl were prepared for each DNA for use in the PCR reactions.

Example 3
Amplification of Polymorphic Microsatellite DNA Markers

PCR amplification and analysis of polymorphic simple sequence repeats (microsatellites) from genomic DNA prepared according to Example 2 was carried out using a modification of the method of Weber and May, *Am. J. Hum. Genet.* 44:388–396 (1989). The primers were either purchased or were synthesized by the phosphoramidite method described by Beaucage and Carruthers, *Tetr. Lett.* 22:1859–1862 (1981), or by the triester method, according to Matteucci et al., *J. Am. Chem. Soc.* 103:3185 (1981).

PCR was carried out using a MJ Research thermocycler. Each 10 μl reaction contained 20 ng of genomic DNA template, 1 to 2 units of Taq polymerase (Boehringer Mannheim), 0.1 to 4 μM each primer, 10 mM tris, pH 8.3, 50 mM KCl, 1.5 mM $MgCl_2$ 200 mM dNTP's, 1 to 3 μCi α-32P -dCTP at 300 Ci/mmole. PCR amplification consisted of 25 to 28 cycles of 1 minute denaturation at 94° C., 1 minute annealing at 55° C., and 1 minutes extension at 72° C. An initial denaturation at 95° C. for two minutes and a final extension at 72° C. for six minutes were also included. An aliquot of each PCR reaction was mixed with 0.8 volumes of 95% formamide, heat denatured, and electrophoresed in a 6% polyacrylamide sequencing gel. Gels were dried under vacuum and exposed to Kodak X-OMat AR film from 16 to 48 hours. Allele sizes were determined by comparison with a standard M13 sequence reaction.

Example 4

Linkage Analysis

The cosegregation of polymorphic markers (see Table 3) with the depression phenotype was analyzed for the 10 families noted in Example 1. The data were subjected to an affected sib-pairs analysis as described in Terwilliger & Ott, *Handbook of Human Genetic Linkage* (Johns Hopkins, MD, 1994), Ch. 26. This approach requires no assumptions to be made concerning penetrance or variant frequency, but only takes into account the data of a relatively small proportion (i.e., the SIB pairs) of all the family members whose phenotype and polymorphic markers have been determined. Specifically, the SIB pairs analysis scores each pair of affected SIBS as sharing (concordant) or not sharing (discordant) the same allelic variant of each polymorphic marker. For each marker, a probability is then calculated that the observed ratio of concordant to discordant SIB pairs would arise without linkage of the marker. Table 4 shows the data from this analysis for the same families and same markers as described above. The data indicate a high probability that markers D19S216, D19S177, INSR, D19S76 and D19S391 are linked to dep.

TABLE 3

Human Chromosome19 Multiallelic Microsatellite Markers

| Locus | Gene | PIC | Reference |
|---|---|---|---|
| D19S247 | DNA segment | 0.79 | GDB Human Genome Data Base, John Hopkins University |
| D19S216 | DNA segment | 0.76 | Nature 359: 794–801, 1992 |
| D19S177 | DNA segment | 0.79 | GDB Human Genome Data Base, John Hopkins University |
| D19S406 | DNA segment | 0.70 | GDB Human Genome Data Base, John Hopkins University |
| INSR | Insulin Receptor | 0.55 | Nucleic Acid Res. 19: 5094; 1991 |
| D19S76 | DNA segment | 0.50 | Nucleic Acid Res. 18: 2835, 1990 |
| D19S391 | DNA segment | 0.80 | GDB Human Genome Data Base, John Hopkins University |
| D19S413 | DNA segment | 0.78 | GDB Human Genome Data Base, John Hopkins University |
| D19S394 | DNA segment | 0.80 | GDB Human Genome Data Base, John Hopkins University |
| D19S221 | DNA segment | 0.87 | Nature 359: 794–801, 1992 |
| D19S179 | DNA segment | 0.68 | GDB Human Genome Data Base, John Hopkins University |
| D19S226 | DNA segment | 0.86 | Nature 359: 794–801, 1992 |
| D19S252 | DNA segment | 0.70 | GDB Human Genome Data Base, John Hopkins University |
| D19S244 | DNA segment | 0.88 | GDB Human Genome Data Base, John Hopkins University |
| D19S199 | DNA segment | 0.83 | GDB Human Genome Data Base, John Hopkins University |
| D19S212 | DNA segment | 0.68 | Nature 359: 794–801, 1992 |
| D19S384 | DNA segment | 0.57 | GDB Human Genome Data Base, John Hopkins University |
| D19S75 | DNA segment | 0.64 | GDB Human Genome Data Base, John Hopkins University |

TABLE 4

Affected SIB Pairs Analysis

| Map Location | Marker  | Concordant | Discordant | p Value    |
|--------------|---------|------------|------------|------------|
| 0            | D19S247 | 15         | 4          | $p < 0.03$   |
| 6            | D19S216 | 18         | 1          | $p < 0.001$  |
| 10           | D19S177 | 18         | 1          | $p < 0.001$  |
| 12           | INSR    | 19         | 0          | $p < 0.0002$ |
| 15           | D19S76  | 19         | 0          | $p < 0.0002$ |
| 18           | D19S391 | 17         | 2          | $p < 0.004$  |
| 23           | D19S394 | 9          | 10         | n.s.       |
| 30           | D19S244 | 8          | 11         | n.s.       |

Figures 1, 1G:
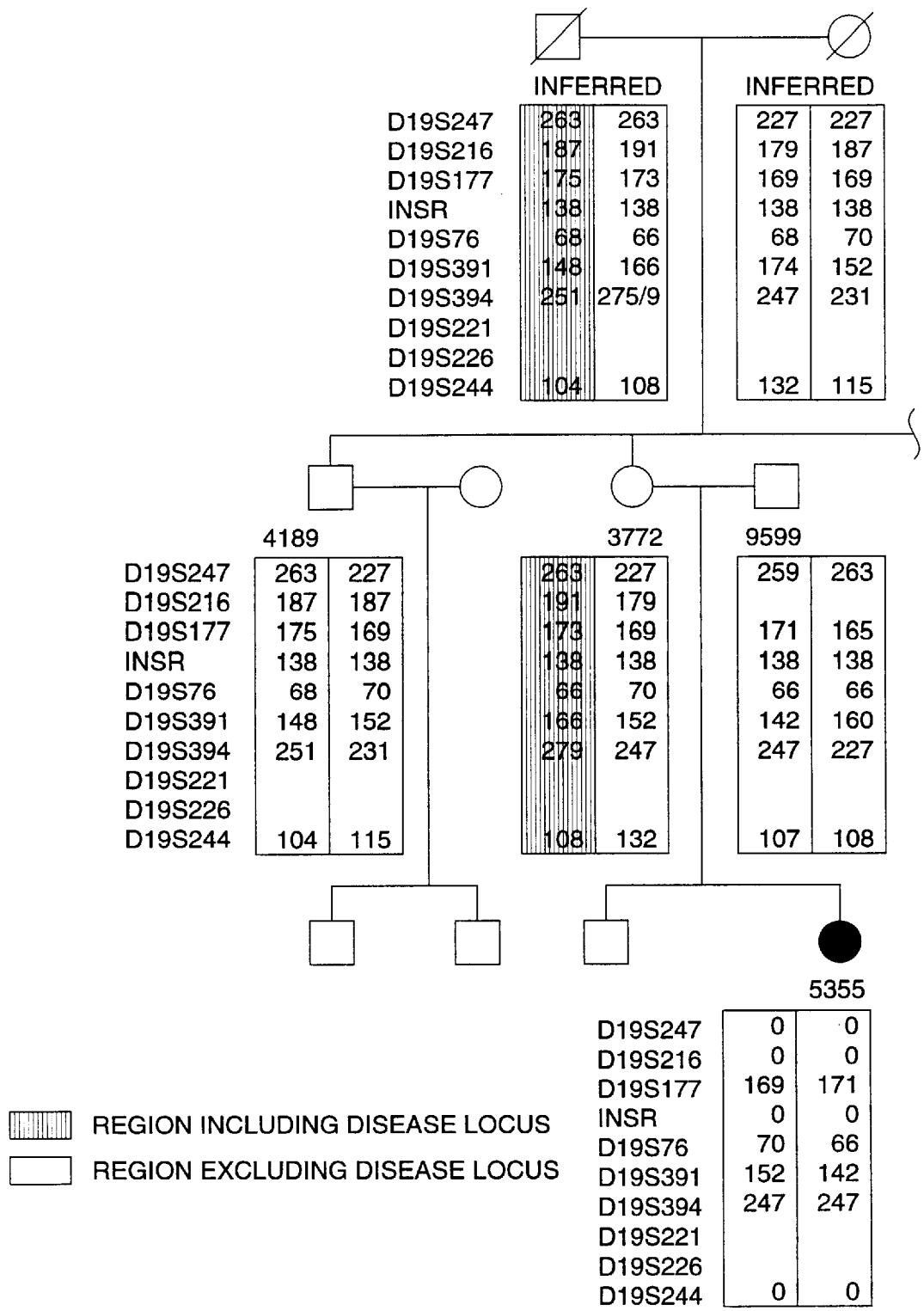
Figures 1, 1G, 2:
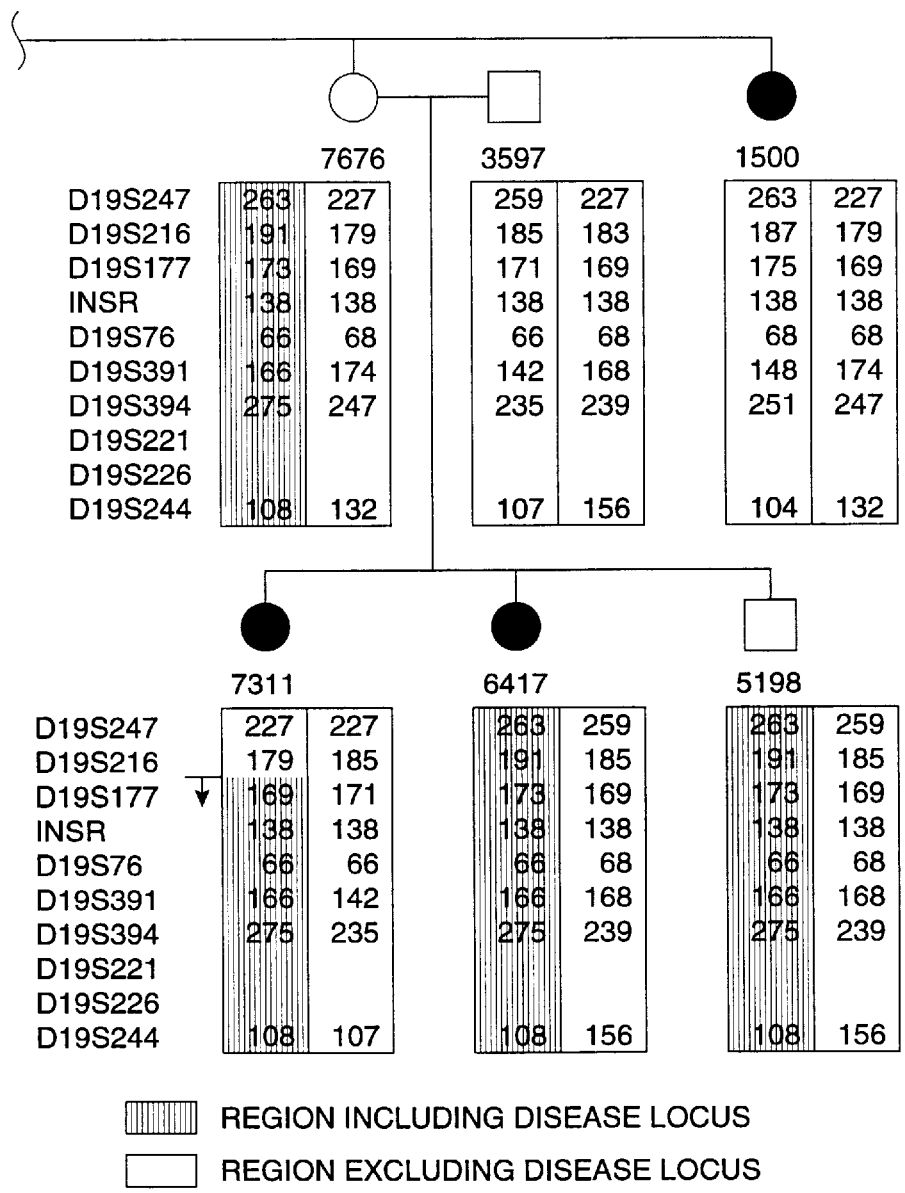
Figures 1, 1H:
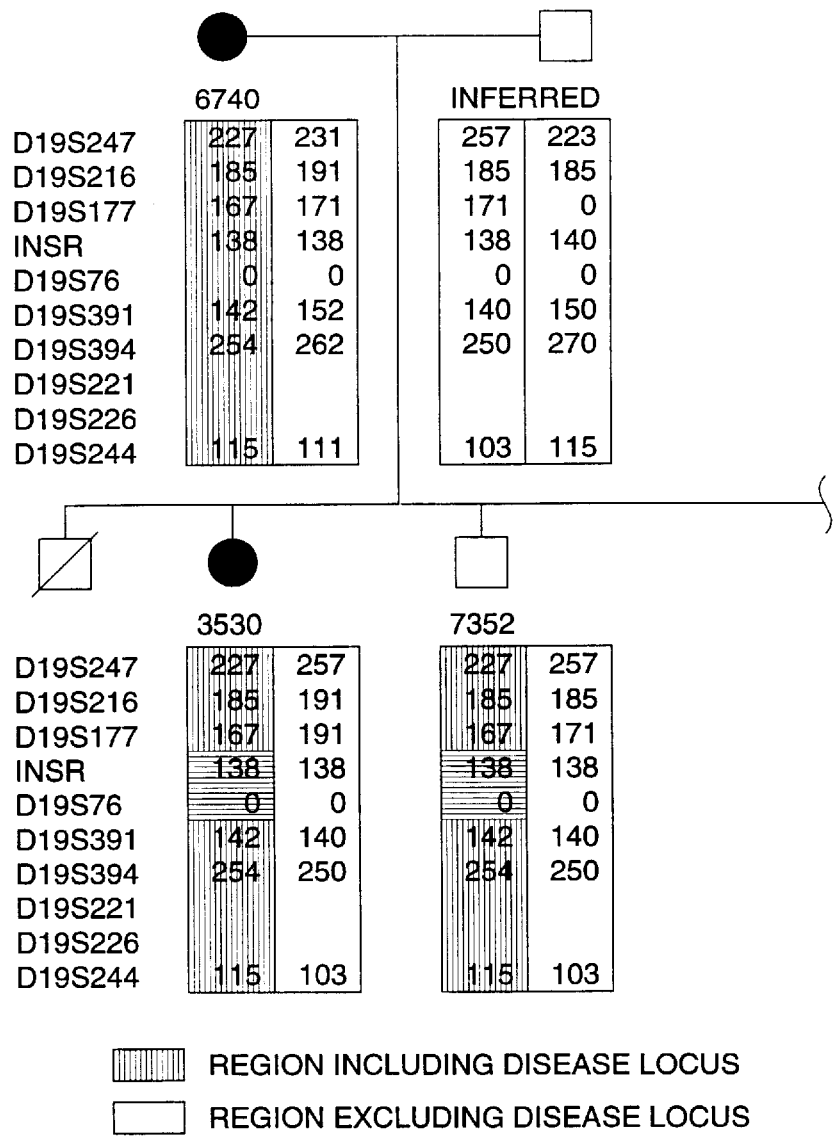
Figures 1, 1H, 2:
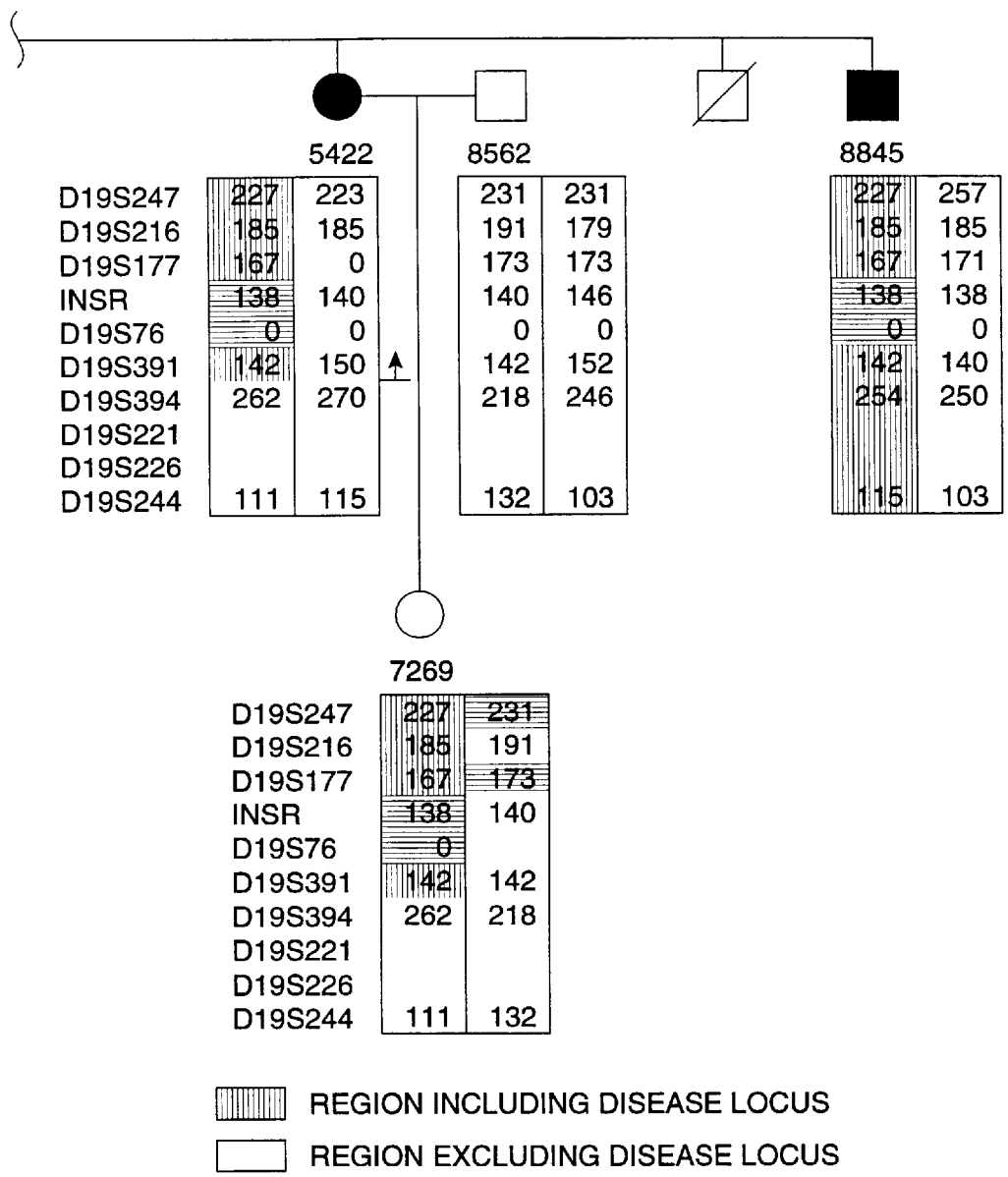
Figures 1, 1I:
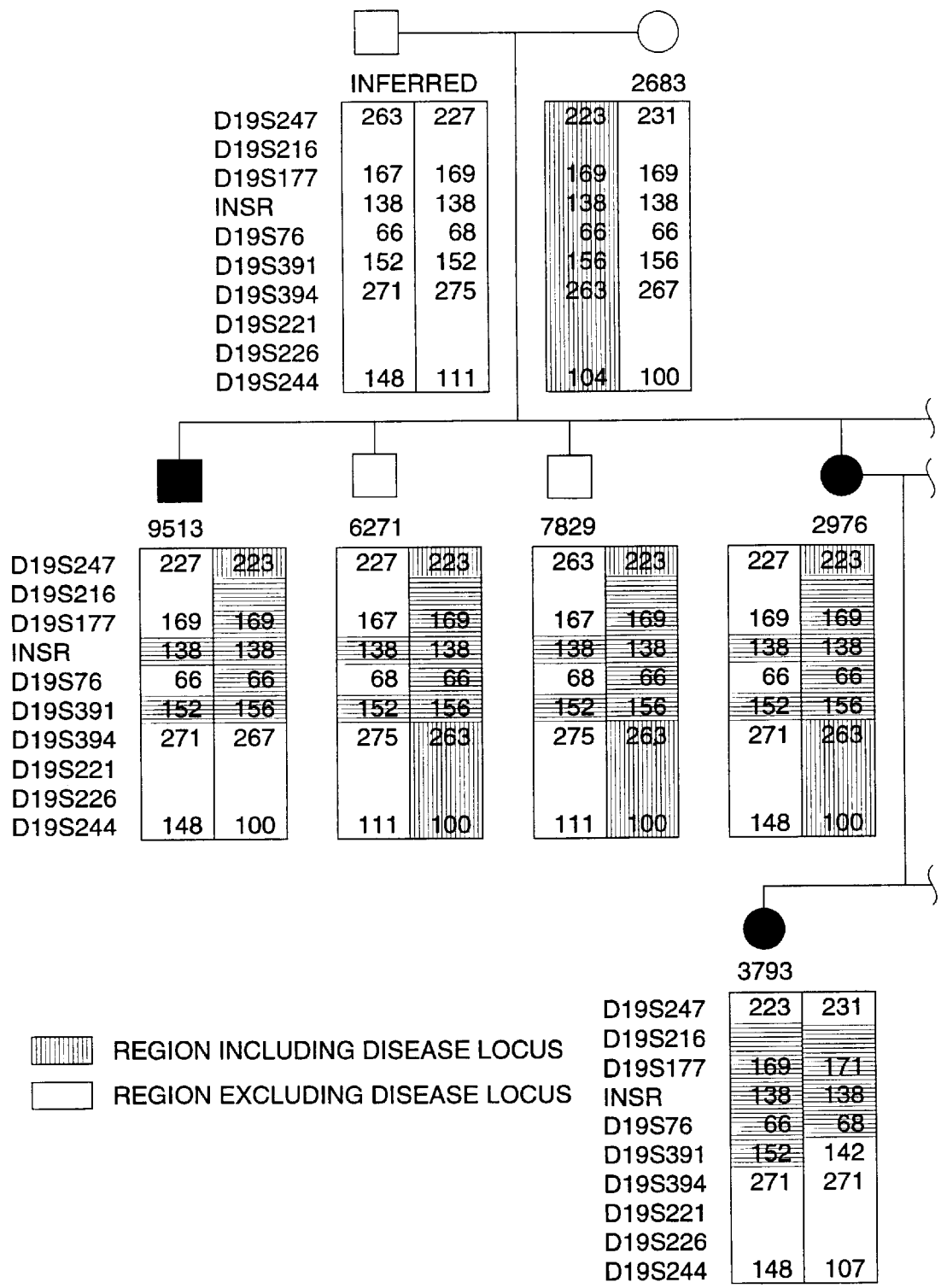
Figures 2, 11:
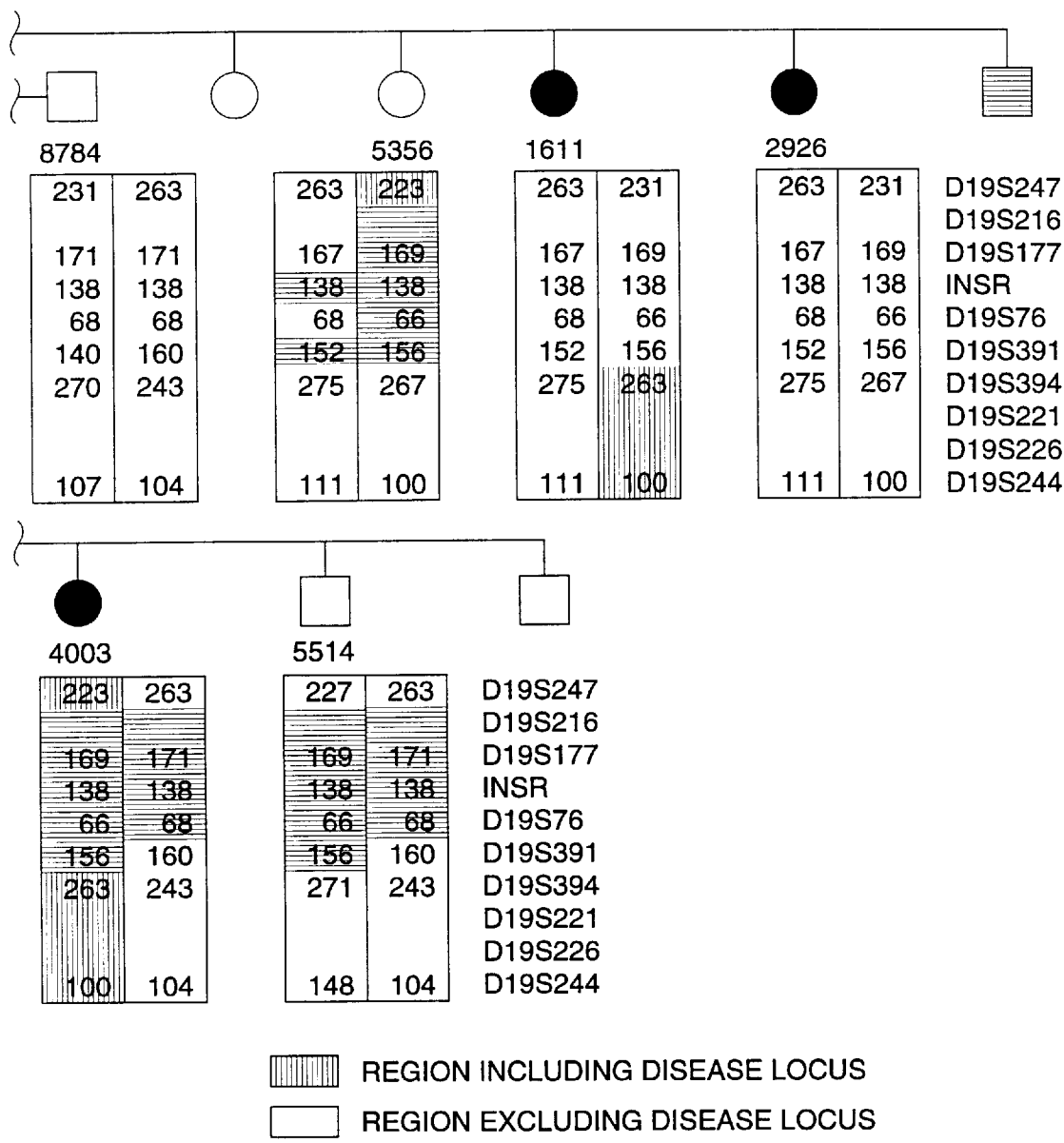
Figures 1, 1J:
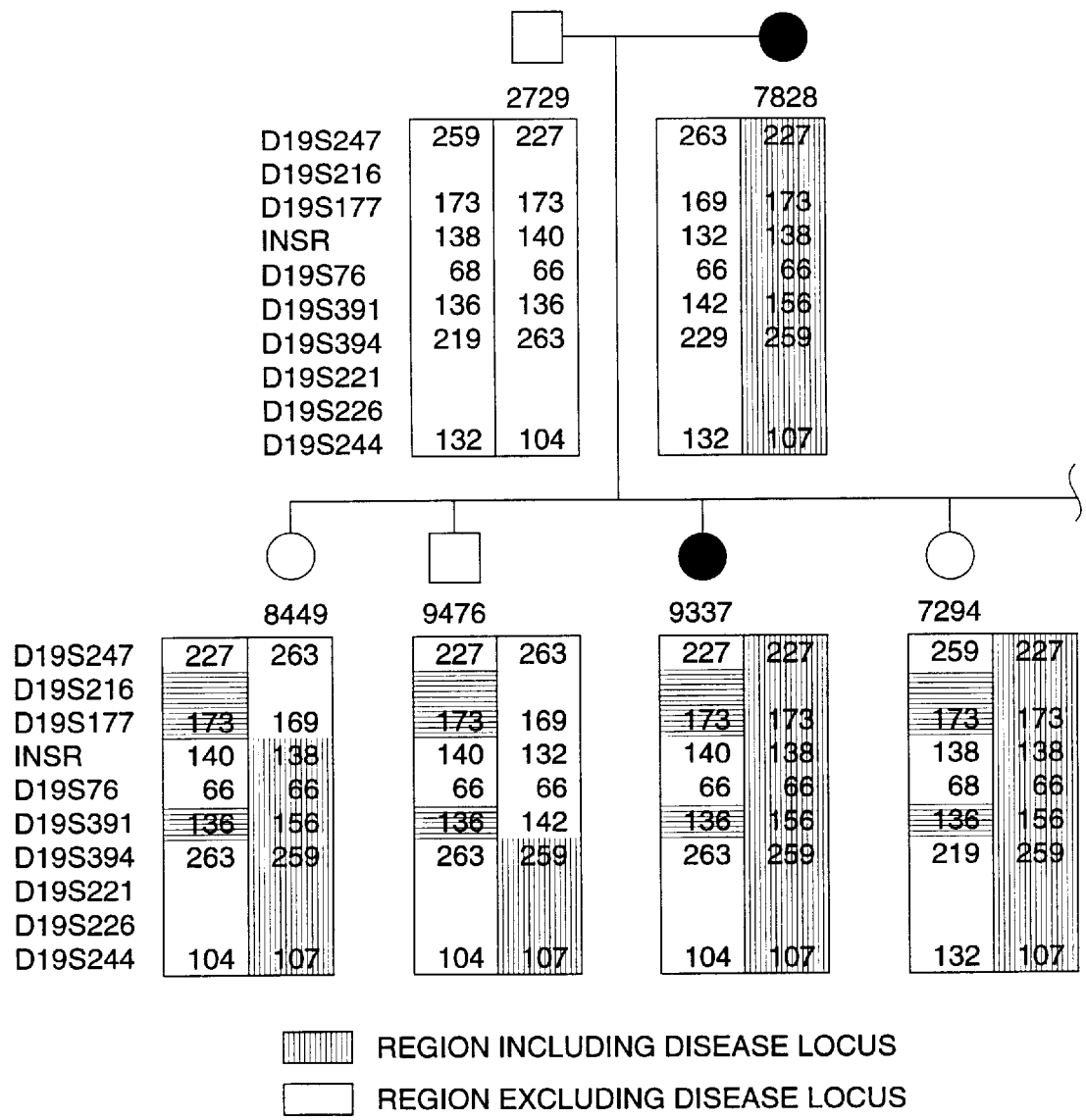
Figures 1, 1J, 2:
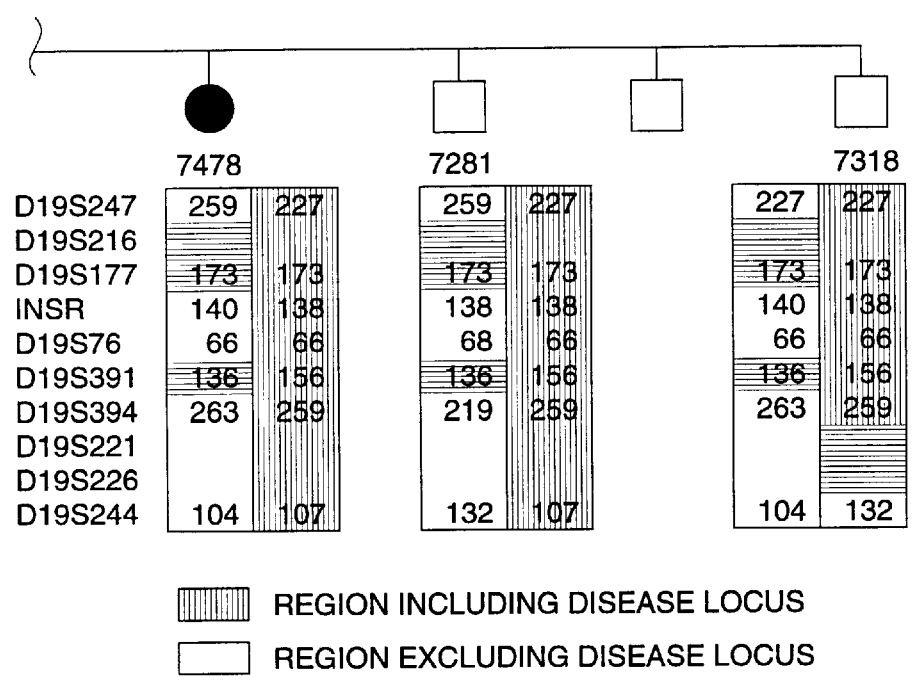

The data have also been subjected to haplotype analysis. This analysis assigns allelic markers between the chromosomes of an individual such that the number of recombinational events needed to account for segregation between generations is minimized. In FIG. 1 (panels A–J) illustrating haplotype analysis, boxes represent males and circles represent females. Solid boxes or circles indicate patients or family members who suffer from depression. "271," "231," "267," and "227," for example, represent different allelic variants of the D19S247 marker. Therefore, for example, in Family 22, the two granddaughters 2749 and 3115, share the complete set of markers from the proposed variant chromosome of the grandmother 7360 (nonpenetrant). The son 9896 received the D19S247 marker from her wildtype chromosome and the D19S216, INSR, D19S391, D19S394, D19S221, D19S226 and D19S244 markers from the proposed variant chromosome. Thus, it is deduced that dep is proximal to D19S247. Family 23 reveals that dep is distal to D19S221 (family member 6255 is nonpenetrant). Family 76 reveals that dep is distal to D19S394 (family member 7352 is nonpenetrant). Family 69 reveals that dep is proximal to D19S177. It can be seen that the dep gene is localized to a segment of about 15 cM between markers D19S177 and D19S394. Notably, this segment includes the INSR and D19S76 markers, which showed the highest degree of linkage in the previous analyses.

These data strongly suggest that a gene associated with the phenotype of depression is linked to the D19S216, D19S177, INSR, D19S76 and D19S391 markers. These markers all occur within the chromosome 19p13 region. That these same markers also show linkage to others neurogenetic diseases suggest that the traits of the diseases are closely linked or perhaps coincident loci (see copending applications U.S. Ser. No. 08/366,288 and attorney docket # 016351-001000).

The pattern of segregation of the disease within the families also serves to confirm the mode of inheritance is autosomal dominant. For example, about half of the progeny resulting from mating between one affected parent and one unaffected parent have the disease, as predicted.

The foregoing description of the preferred embodiments of the present invention has been presented for purposes of illustration and description. They are not intended to be exhaustive or to limit the invention to the precise form disclosed, and many modifications and variations are possible in light of the above teaching. All publications and patent applications cited herein are incorporated by reference in their entirety to the same extent as if each individual publication or patent application was specifically and individually so denoted.

---

A: CLINICAL DEPRESSION INTERVIEW

1. Have you ever had a time when you felt sad or depressed for most of the day, nearly every day?
   No    Yes: How long did it last? Did it ever last as long as 2 weeks?
             <2 weeks    ≧2 weeks
2. Has there ever been a time when you lost interest in things you used to enjoy?
   No    Yes: How long did it last? Did it ever last as long as 2 weeks?
             <2 Weeks    >2 weeks

[IF NO TO BOTH OF ABOVE, SKIP TO FAMILY HISTORY]
NOW I WOULD LIKE TO ASK YOU SOME QUESTIONS ABOUT THE WORST TIME.

3. a. During that time, how was your appetite ?    Unchanged    Increase    Decrease    [MUST BE NEARLY EVERY DAY]
   [or]
   b. Did you Lose/Gain weight? How much? Were you trying to?    No    Yes
   [MUST BE >5% OF BODY WEIGHT IN ONE MONTH]
4. Did you have any changes in your sleep habits, such as trouble falling asleep, waking up too early or sleeping too much?    No    Yes
5. Did you have any problem with feeling fidgety or restless ? What about the opposite-did you find that you were talking or moving more slowly than usual?    No    Yes
6. Did you notice decreased energy , fatigue or a feeling of being tired all the time?    No    Yes
7. How did you feel about yourself? (Did you feel worthless or guilty ?)    No    Yes
8. Did you have any trouble concentrating or making decisions?    No    Yes
9. Were things ever so bad, that you were thinking about death or that you would be better off dead?    No    Yes

[5 OF 9 SYMPTOMS MUST BE PRESENT]

10. a. Just before this time began, were you physically ill?    No    Yes
    b. Were you taking any medications, drugs or alcohol?    No    Yes
    c. Did this begin soon after someone close to you died?    No    Yes

| | |
|---|---|
| A: CLINICAL DEPRESSION INTERVIEW | |
| 11. How many episodes like this have you had? | |
| 12. How old were you when you first had an episode like this? | |
| 13. When did you last have an episode like this? | _____ (age in years) |
| 14. Have you ever had a time when you felt the opposite--when you felt so good or hyper that you were not yourself? A time when you needed less sleep than usual, your thoughts were racing or you did things that could cause trouble for you or your family?<br>    No            Yes | |
| 15. Have you ever seen a doctor or counselor for depression?<br>    Yes | No |
| 16. Have you ever taken any medication for depression?<br>    Yes<br>    Medication/Effect: _____ | No |
| 17. Have you ever had counseling or any other treatment for depression?<br>Yes | No |
| 18. Is there anything that has repeatedly contributed to your depression? (Seasonal, pregnancy, PMS, etc.)<br>    No     Yes--Describe: | |
| 19. Has depression interfered with important aspects of your life, such as personal relationships, school, employment, finances or health?<br>    No     Yes--Describe: | |
| [FAMILY HISTORY] Does anyone in your family have problems with depression?<br>Parents:              Siblings:<br>Spouse/children: | |
| 20. Have you or anyone else in your family ever attempted/committed suicide?<br>Yes | No |

What is claimed is:

1. A method of diagnosing susceptibility to depression in a patient, the method comprising:

determining the presence or absence of an allele of a polymorphic marker in the DNA of the patient, wherein the polymorphic marker is within a segment of chromosome 19p13 bordered by D19S247 and D19S394 and is linked to a DNA segment (dep) having a variant form associated with a phenotype of depression, and the allele is in phase with the variant form of dep, whereby the presence of the allele in the patient indicates susceptibility to depression.

2. The method of claim 1, wherein the polymorphic marker is INSR, D19S76 or D19S391.

3. The method of claim 1, wherein the polymorphic marker is within 5 cM of the D19S76 marker.

4. The method of claim 1, wherein the polymorphic marker is between INSR and D19S391.

5. The method of claim 1, wherein the allele is in linkage disequilibrium with the DNA segment.

6. The method of claim 1, further comprising the step of establishing that the allele is in phase with the variant form of the DNA segment.

7. The method of claim 6, wherein the establishing step comprises determining the presence or absence of the allele in first and second relatives of the patient, the first and second relative each being of known phenotype for depression, at least one of the relatives having a phenotype of depression and being heterozygous for the allele.

8. The method of claim 7, further comprising the step of determining the phenotypes of relatives.

9. The method of claim 8, wherein the phenotypes of the relatives are determined by the DSM-IV criteria of Table 1.

10. The method of claim 9, wherein one of the relatives is a parent of the patient.

11. The method of claim 1, further comprising the step of determining the presence or absence of an allele of a second polymorphic marker in the patient.

12. The method of claim 1, wherein the presence or absence of the allele is determined by amplifying a segment of DNA within chromosome 19p13 that spans the polymorphic marker.

13. The method of claim 12, further comprising the step of determining the size of the amplified segment.

14. The method of claim 12, further comprising the step of determining the sequence of the amplified segment.

15. The method of claim 12, further comprising the step of determining the presence or absence of a restriction enzyme site within the amplified segment.

16. The method of claim 1, wherein the presence or absence of the allele is determined by contacting the DNA from the patient with an oligonucleotide probe capable of hybridizing to the allele under stringent conditions;

determining whether hybridization has occurred thereby indicating the presence of the allele.

17. The method of claim 16, further comprising the step of isolating a sample of DNA from the patient.

18. The method of claim 17, wherein the DNA is genomic and the sample is obtained from saliva, blood or buccal mucosal cells.

19. The method of claim 1, further comprising the step of informing the patient or a treating physician of the susceptibility of the patient to depression.

* * * * *